US010568709B2

(12) United States Patent
Beira

(10) Patent No.: US 10,568,709 B2
(45) Date of Patent: Feb. 25, 2020

(54) MECHANICAL TELEOPERATED DEVICE FOR REMOTE MANIPULATION

(71) Applicant: DistalMotion SA, Lausanne (CH)

(72) Inventor: Ricardo Daniel Rita Beira, Lausanne (CH)

(73) Assignee: Distalmotion SA, Epalinges (CH)

(*) Notice: Subject to any disclaimer, the term of this patent is extended or adjusted under 35 U.S.C. 154(b) by 0 days.

(21) Appl. No.: 15/564,193

(22) PCT Filed: Apr. 11, 2016

(86) PCT No.: PCT/IB2016/000543
§ 371 (c)(1),
(2) Date: Oct. 3, 2017

(87) PCT Pub. No.: WO2016/162752
PCT Pub. Date: Oct. 13, 2016

(65) Prior Publication Data
US 2018/0125592 A1    May 10, 2018

Related U.S. Application Data

(60) Provisional application No. 62/145,452, filed on Apr. 9, 2015.

(51) Int. Cl.
*A61B 34/37* (2016.01)
*A61B 17/00* (2006.01)
(Continued)

(52) U.S. Cl.
CPC ........ *A61B 34/37* (2016.02); *A61B 17/00234* (2013.01); *A61B 34/71* (2016.02);
(Continued)

(58) Field of Classification Search
CPC ......... A61B 34/37; A61B 34/77; A61B 34/71; A61B 2034/715; A61B 2090/506; A61B 17/00234; B25J 18/007; B25J 3/02
(Continued)

(56) References Cited

U.S. PATENT DOCUMENTS 2,764,301 A    9/1956    Goertz et al.
2,771,199 A    11/1956   Jelatis
(Continued)

FOREIGN PATENT DOCUMENTS

CN    101584594 A    11/2009
CN    101637402 A    2/2010
(Continued)

OTHER PUBLICATIONS

US 9,232,978 B2, 01/2016, Shellenberger et al. (withdrawn)
(Continued)

*Primary Examiner* — Ziaul Karim
(74) *Attorney, Agent, or Firm* — Eversheds Sutherland (US) LLP; Christopher C. Bolten; Albert K. Heng

(57) ABSTRACT

A mechanical teleoperated device for remote manipulation is provided that is primarily intended for use in minimally invasive surgery. The device generally comprises a slave unit having a number of slave links interconnected by a plurality of slave joints, an end-effector connected to the distal end of the slave unit, a master unit having a corresponding number of master links interconnected by a plurality of master joints, and a handle connected to the distal end of the master unit for operating the mechanical teleoperated device. The device further comprises mechanical transmission means arranged to kinematically connect the slave unit with the master unit such that the movement applied on each master joint of the master unit is reproduced by the corresponding slave joint of the slave unit. In addi- (Continued)

tion, the mechanical teleoperated device comprises improved kinematics and an improved arrangement of mechanical constraints, allowing for improved positioning of the device over a patient, increased workspace inside the patient and ease of workflow in an operating room.

12 Claims, 21 Drawing Sheets

(51) Int. Cl.
  *B25J 3/02* (2006.01)
  *B25J 18/00* (2006.01)
  *A61B 34/00* (2016.01)
  *A61B 90/50* (2016.01)
(52) U.S. Cl.
  CPC ............ *A61B 34/77* (2016.02); *B25J 3/02* (2013.01); *B25J 18/007* (2013.01); *A61B 2034/715* (2016.02); *A61B 2090/506* (2016.02)
(58) Field of Classification Search
  USPC ....................................................... 700/3, 12
  See application file for complete search history.

(56) References Cited

U.S. PATENT DOCUMENTS

| | | |
|---|---|---|
| 2,774,488 A | 12/1956 | Goertz |
| 2,846,084 A | 8/1958 | Goertz et al. |
| 3,065,863 A | 11/1962 | Saunders, Jr. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |

(56) References Cited

U.S. PATENT DOCUMENTS

| | | |
|---|---|---|
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,602,287 B2 | 12/2013 | Yates et al. |
| 8,603,077 B2 | 12/2013 | Cooper et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,861 B2 | 8/2015 | Martin et al. |
| 9,149,339 B2 | 10/2015 | Unsworth |
| 9,204,939 B2 | 12/2015 | Frimer et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1* | 6/2007 | Devengenzo ............ B25J 15/04 74/490.01 |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0314181 A1 | 12/2008 | Schena |
| 2009/0036902 A1 | 2/2009 | Dimaio et al. |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0299141 A1 | 12/2009 | Downey et al. |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |

(56) References Cited

U.S. PATENT DOCUMENTS

| | | |
|---|---|---|
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0304083 A1 | 11/2013 | Kaercher et al. |
| 2013/0304084 A1* | 11/2013 | Beira ............... F16H 19/08 606/130 |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1* | 7/2014 | Beira ............ A61B 17/00234 700/3 |
| 2014/0200561 A1 | 7/2014 | Ingmanson et al. |
| 2014/0207150 A1 | 7/2014 | Rosa et al. |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1* | 9/2014 | Smaby ............... A61B 34/30 606/130 |
| 2014/0276951 A1* | 9/2014 | Hourtash ......... A61B 19/2203 606/130 |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0346053 A1 | 12/2016 | Beira |
| 2016/0374766 A1 | 12/2016 | Schuh |
| 2017/0245954 A1 | 8/2017 | Beira |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0028269 A1 | 2/2018 | Morel et al. |
| 2018/0055583 A1 | 3/2018 | Schuh et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 0 776 739 A2 | 6/1997 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 783 643 A1 | 10/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 834 244 | 5/1960 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-97/43942 A1 | 11/1997 |
| WO | WO-98/25666 A1 | 6/1998 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/025818 A1 | 3/2011 |
| WO | WO-2011/027183 A2 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/007784 A1 | 1/2013 |
| WO | WO-2013/014621 A2 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 A1 | 6/2014 |
| WO | WO-2014/094718 A1 | 6/2014 |
| WO | WO-2014/094719 A1 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |

(56) References Cited

FOREIGN PATENT DOCUMENTS

| | | |
|---|---|---|
| WO | WO-2015/175200 A1 | 11/2015 |
| WO | WO-2016/030767 A9 | 3/2016 |
| WO | WO-2016/083189 A1 | 6/2016 |
| WO | WO-2016/097861 A1 | 6/2016 |
| WO | WO-2016/097864 A2 | 6/2016 |
| WO | WO-2016/097868 A1 | 6/2016 |
| WO | WO-2016/097871 A1 | 6/2016 |
| WO | WO-2016/097873 A2 | 6/2016 |
| WO | WO-2016/154173 A1 | 9/2016 |
| WO | WO-2016/162751 A1 | 10/2016 |
| WO | WO-2016/162752 A1 | 10/2016 |
| WO | WO-2016/183054 A1 | 11/2016 |
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |
| WO | WO-2017/220978 A1 | 12/2017 |
| WO | WO-2018/142112 A1 | 8/2018 |
| WO | WO-2018/162921 A1 | 9/2018 |

OTHER PUBLICATIONS

Abbott, et al., "Design of an Endoluminal Notes Robotic System," IEEE/RSJ International Conference on Intelligent Robots and Systems, San Diego, CA, pp. 410-416 (2007).
Aesculap Surgical Technologies, Aesculap® Caiman®, Advanced Bipolar Seal and Cut Technology Brochure, 6 pages (retrieved Aug. 31, 2015).
Arata, et al., "Development of a dexterous minimally-invasive surgical system with augmented force feedback capability," IEEE/RSJ International Conference on Intelligent Robots and Systems, pp. 3207-3212 (2005).
Çavuşoğlu, et al., "Laparoscopic Telesurgical Workstation," IEEE Transactions on Robotics and Automation,(15)4:728-739 (1999).
Charles, et al., Dexterity-enhanced Telerobotic Microsurgery, Advanced Robotics, ICAR '97. Proceedings, 8th Int'l Conference (1997).
Dachs, et al., "Novel Surgical Robot Design: Minimizing the Operating Envelope Within the Sterile Field," 28th International Conference, IEEE Engineering in Medicine Biology Society, New York, pp. 1505-1508 (2006).
Dario, et al., "Novel Mechatronic Tool for Computer-Assisted Arthroscopy," IEEE Transactions on Information Technology in Biomedicine, 4(1):15-29 (Mar. 2000).
Focacci, et al., "Lightweight Hand-held Robot for Laparoscopic Surgery," IEEE International Conference on Robotics & Automation, Rome, Italy, pp. 599-604 (2007).
Guthart, et al., "The Intuitive™ Telesurgery System: Overview and Application," IEEE International Conference on Robotics & Automation, San Francisco, CA, pp. 618-621 (2000).
Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).
Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).
International Search Report & Written Opinion dated Feb. 2, 2017 in Int'l PCT Patent Appl. Serial No. PCT/IB2016/001286.
International Search Report & Written Opinion dated Jan. 18, 2013 in Int'l PCT Patent Appl Serial. No. PCT/IB2012/053786.
International Search Report dated Jan. 18, 2013 in Int'l PCT Patent Appl Serial No. PCT/IB2012/053786.
International Search Report dated Mar. 23, 2012 in Int'l PCT Patent Appl Serial. No. PCT/IB2011/054476.

Ishii, et al., "Development of a New Bending Mechanism and Its Application to Robotic Forceps Manipulator," IEEE International Conference on Robotics & Automation, Rome, Italy, pp. 238-243 (2007).
International Search Report & Written Opinion dated Feb. 17, 2016 in Int'l PCT Patent Appl Serial No. PCT/IB2015/002095.
International Search Report & Written Opinion dated May 23, 2016 in Int'l PCT Patent Appl Serial No. PCT/IB2015/002524.
International Search Report & Written Opinion dated Mar. 23, 2012 in Int'l PCT Patent Appl Serial No. PCT/IB2011/054476.
International Search Report & Written Opinion dated Mar. 30, 2015 in Int'l PCT Patent Appl Serial No. PCT/EP2015/051473.
International Search Report & Written Opinion dated Apr. 26, 2016 in Int'l PCT Patent Appl Serial No. PCT/IB2015/002512.
International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2016/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Lang, et al., Intra-operative robotics: NeuroArm., Acta Neurochir Suppl, 109:231-236 (2011).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Mitsuishi, et al., Master-slave robotic platform and its feasibility study for micro-neurosurgery, Int. J. Med. Robot., 9(2):180-9 (2013).
Morita, et al., Microsurgical robotic system for the deep surgical field: development of a prototype and feasibility studies in animal and cadaveric models, J. Neurosurg., 103(2):320-7 (2005).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker®, Endoscopy, Take a Look Around, Ideal Eyes™ FFD122 HD, Articulating Laparoscope Brochure, 2 pages (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).

(56) References Cited

OTHER PUBLICATIONS www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery—Robotic and Image-Guided Surgery, Ibaraki, Japan, 4 pages (2005).
Zeus, "Robotic Surgical System" available at http://al-laboutroboticsurgery.com/zeusrobot.html.
U.S. Appl. No. 13/878,924, filed May 17, 2013.
U.S. Appl. No. 14/233,184 / U.S. Pat. No. 9,696,700, filed Jan. 16, 2014 / Jul. 4, 2017.
U.S. Appl. No. 15/116,509, filed Aug. 3, 2016.
U.S. Appl. No. 15/506,659, filed Feb. 24, 2017.
U.S. Appl. No. 15/536,539, filed Jun. 15, 2017.
U.S. Appl. No. 15/536,562, filed Jun. 15, 2017.
U.S. Appl. No. 15/536,568, filed Jun. 15, 2017.
U.S. Appl. No. 15/536,573, filed Jun. 15, 2017.
U.S. Appl. No. 15/536,576, filed Jun. 15, 2017.
U.S. Appl. No. 15/564,194, filed Oct. 3, 2017.
U.S. Appl. No. 15/633,611, filed Jun. 26, 2017.
International Search Report & Written Opinion dated Jul. 10, 2018 in Int'l PCT Patent Appl. Serial No. PCT/IB2018/053272.
Communication Relating to the Results of the Partial International Search dated May 28, 2019 in Int'l PCT Patent Appl. Serial No. PCT/IB2019/050961.

* cited by examiner

MECHANICAL TELEOPERATED DEVICE FOR REMOTE MANIPULATION

CROSS-REFERENCE TO RELATED APPLICATIONS

This application is a national phase of International PCT Patent Application No. PCT/IB2016/000543, filed Apr. 11, 2016, which claims priority to U.S. Provisional Patent Application No. 62/145,452, filed Apr. 9, 2015, the entire contents of each of which are incorporated herein by reference.

FIELD OF THE INVENTION

The present invention relates to the field of remotely actuated mechanical systems and more particularly to a mechanical teleoperated device for remote manipulation for use primarily in minimally invasive surgical procedures, using small size access incisions into the patient body. Specifically, the present invention relates to a mechanical teleoperated device with improved kinematics and arrangement of constraints allowing for better positioning of the device over a patient, increased workspace inside the patient and better integration into operating room workflow. This device is also adapted for any suitable remote actuated application requiring a dexterous manipulation with high stiffness, precision and quality force feedback such as assembly manipulation, manipulation in narrow places, manipulation in dangerous or difficult environments, and manipulation in contaminated or clean environments.

BACKGROUND OF THE INVENTION

Open surgery is still the standard technique for most surgical procedures. It has been used by the medical community for several decades and consists of performing the surgical tasks by a long incision in the abdomen, through which traditional surgical tools are inserted. However, due to the long incision, this approach is extremely invasive for the patients, resulting in substantial blood loss during the surgery and long and painful recovery periods at the hospital.

In order to reduce the invasiveness of open surgery, laparoscopy, a minimally invasive technique, was developed. Instead of a single long incision, four to five small incisions are made in the patient through which long and thin surgical instruments and endoscopic cameras are inserted. Because of the low invasiveness, this technique reduces blood loss and shortens hospital stays and pain. When performed by experienced surgeons, this technique can attain clinical outcomes similar to open surgery. However, despite the above-mentioned advantages, laparoscopy requires extremely advanced surgeon skills to manipulate the rigid and long instrumentation. The entry incision acts as a point of rotation, decreasing the freedom for positioning and orientating the instruments inside the patient. The movements of the surgeon's hand about this incision are inverted and scaled-up relative to the instrument tip ("fulcrum effect"), which removes dexterity, sensibility and magnifies the tremors of the surgeon's hands. In addition, these long and straight instruments force the surgeons to work in a uncomfortable posture for hands, arms and body, which can be tremendously tiring during several hours of operation. Therefore, due to these drawbacks of the laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of a remote laparoscopy where the surgeon sits at a console manipulating two master manipulators to perform the operation through several small incisions. Like laparoscopy, the robotic approach is also minimally invasive, bringing several advantages over open surgery in terms of pain, blood loss, and recovery time. In addition, it also offers better ergonomy for the surgeon compared to open and laparoscopic techniques. However, although being technically easier, Robotic Surgery brings several negative aspects. A major disadvantage of these systems is related with the extremely high complexity of the existing robotic devices, which are composed by complex mechatronic systems, leading to huge costs of acquisition and maintenance, which are not affordable for the majority of surgical departments worldwide. Another drawback of these systems comes from the fact that current surgical robots are voluminous, competing for precious space within the operating room environment and significantly increasing preparation time. Access to the patient is thus impaired, which, together with the lack of force-feedback, raises safety concerns.

WO9743942, WO9825666 and US2010011900 disclose a robotic tele-operated surgical instrument, designed to replicate surgeons' hand movements inside the patient's body. By means of a computerized, robotic interface, it enables the performance of a remote Laparoscopy where the surgeon sits at a console manipulating two joysticks to perform the operation through several small incisions. However, this system does not have autonomy or artificial intelligence, being essentially a sophisticated tool fully controlled by the surgeon. The control commands are transmitted between the robotic master and robotic slave by a complex computer-controlled mechatronic system, which is extremely costly to produce and maintain and difficult to use by the hospital staff.

WO 2008130235 discloses a less complex mechanical manipulator for an instrument for minimally invasive surgery, having at a proximal end a handle for operating the instrument connected at a distal end of the manipulator. A parallelogram construction is provided between the proximal end and the distal end for guaranteeing an unambiguous position relationship between the handle and the instrument. This parallelogram construction is coupled with a system of bars for controlling the position of the parallelogram construction. The bars of the system are connected to the parallelogram construction as well as to each other by means of cardan joints.

The parallelogram constraint imposed by this mechanical manipulator renders it difficult to obtain a scaled ratio other than 1:1 between the amplitude of the movements applied on the handle of this manipulator and the amplitude of the movements reproduced by the instrument connected at the distal end of the manipulator. This reduces the precision of the manipulator which is at the utmost importance for surgical intervention. In addition, due to the high inertia of the rigid elements of the parallelogram construction, this mechanical manipulator should provide poor haptic transparency to the user. Another issue of this system is related with the fact that the first degree of freedom of the parallelogram needs to be aligned with the incision, which limits the positioning of the manipulator over the surgical table and therefore reduces the number of surgical procedures that can potentially be performed.

Several other mechanical systems have been developed for remote manipulation in radioactive environments and are disclosed in several documents, such as U.S. Pat. No. 2,846,084. However, although the system disclosed in this document comprises a master-slave architecture, its dimensions, weight and kinematics are not suitable for minimally invasive surgical applications.

As disclosed in WO2013014621, the present inventors have already developed a surgical platform that overcomes many of the above-mentioned shortcomings in the known art. However, through continued development, the present inventors have become aware of possible improvements to their prior system that allow for better positioning of the surgical platform over the patient, increased workspace inside the patient and improved workflow in the operating room.

Accordingly, an aim of the present invention is to provide a mechanical teleoperated device preferably for minimally invasive surgical procedures capable of manipulating surgical instruments with higher precision, increased haptic transparency and which overcomes the aforementioned drawbacks of the prior art. The system of the present invention provides for greater maneuverability of the device and better workflow in the operating room even as compared to prior surgical platforms provided by the present inventors.

Another aim of the present invention is to provide a mechanical teleoperated device which can be easily adapted to be used for other forms of minimally invasive surgery as well as open surgery, microsurgery, brain surgery or procedures on MRi environments.

SUMMARY OF THE INVENTION

Theses aims and other advantages are achieved by a mechanical teleoperated device for remote manipulation, designed to naturally replicate the operator's hand movements in the vicinity where manipulations must occur. This mechanical teleoperated device comprises: i) a slave manipulator (referred hereafter as a "slave unit") having a number of slave links interconnected by a plurality of slave joints; ii) an end-effector (instrument/tool or a gripper/holder) connected to the distal end of the slave unit; iii) a master manipululator (referred hereafter as a "master unit") having a corresponding number of master links interconnected by a plurality of master joints; and iv) a handle for operating the mechanical teleoperated device. The mechanical teleoperated device can also be described by considering the end-effector to be part of the slave unit and the handle to be part of the master unit. In a broader sense, the links and joints composing the end-effector can be considered distal slave links and joints, while the links and joints composing the handle can be considered distal master links and joints. The end-effector might be adapted to be releasable from the proximal part of the slave unit.

The mechanical teleoperated device further comprises first mechanical transmission means arranged to kinematically connect the slave unit with the master unit such that the movement (angle of joint) applied on each master joint of the master unit is reproduced by the corresponding slave joint of the slave unit at a predetermined scale ratio, which can advantageously be in the order of 2:1 or 3:1, if each master link is respectively two or three times longer than the corresponding slave link. A scaling down ration of this order of magnitude can significantly improve the precision of the device. In addition, second mechanical transmission means are arranged to kinematically connect the tool or the end-effector with the handle such that the movements applied on the handle are reproduced by the end-effector at a predetermined scaled ratio. The mechanical teleoperated device also comprises mechanical constraint means which are usually configured to ensure that one master link of said master unit is guided or constrained to move along its longitudinal axis so that the corresponding slave link of the slave unit always translates along a virtual axis parallel to the longitudinal axis of said guided master link in the vicinity of the remote manipulation when the mechanical teleoperated device is operated.

As compared to prior surgical platforms described by the present inventors in WO2013014621, the description of which is incorporated by reference herein as if presented herein in full, the mechanical teleoperated system of the present invention has a new kinematic model and a new arrangement of mechanical constraints, whose position in the 3D space can be tuned with respect to the mechanical teleoperated system, allowing for much more flexibility in positioning the mechanical teleoperated system over the patient, while allowing shorter distances between a master and slave manipulator, which results in a lighter and more compact system that can be more easily integrated in the operating room workflow.

BRIEF DESCRIPTION OF FIGURES

The invention will be better understood according to the following detailed description of several embodiments with reference to the attached drawings, in which.

DETAILED DESCRIPTION OF THE INVENTION

Figure 1:
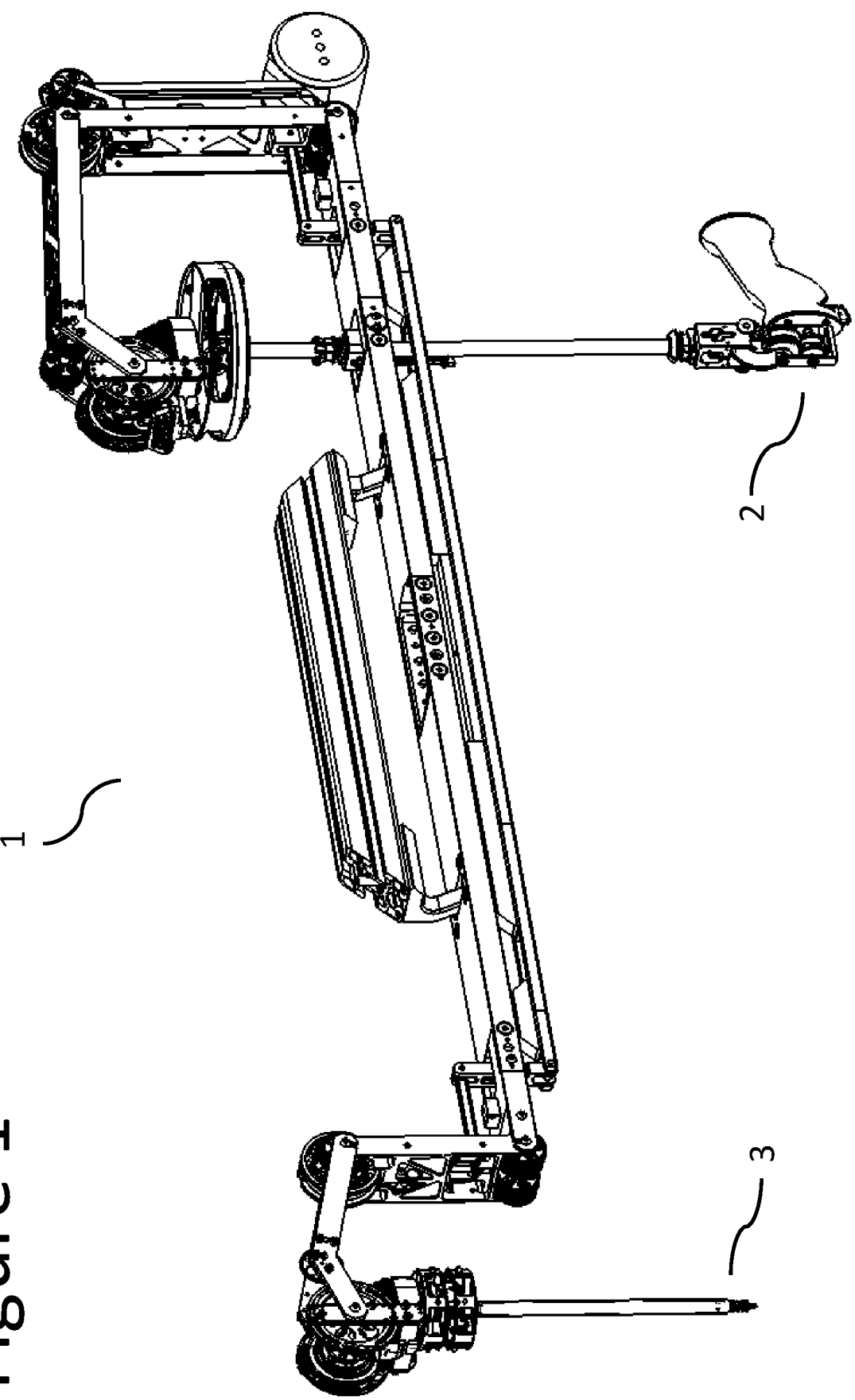
FIG. 1 shows a perspective view of a mechanical telemanipulator according to an embodiment of the invention disclosed in WO2013014621.

The mechanical telemanipulator 34, according to an embodiment of the present invention, is intended to be used in a surgical platform, like the mechanical telemanipulator 1 shown in FIG. 1, whose description is fully disclosed in WO2013014621 and which description is fully incorporated herein by reference as if presented herein in full.

One of the key features of this type of mechanical telemanipulators consists of its master-slave architecture, which enables a natural replication of the user hand movements, on a proximal handle 2, by a distal end-effector 3 on a remote location.

Figure 2:
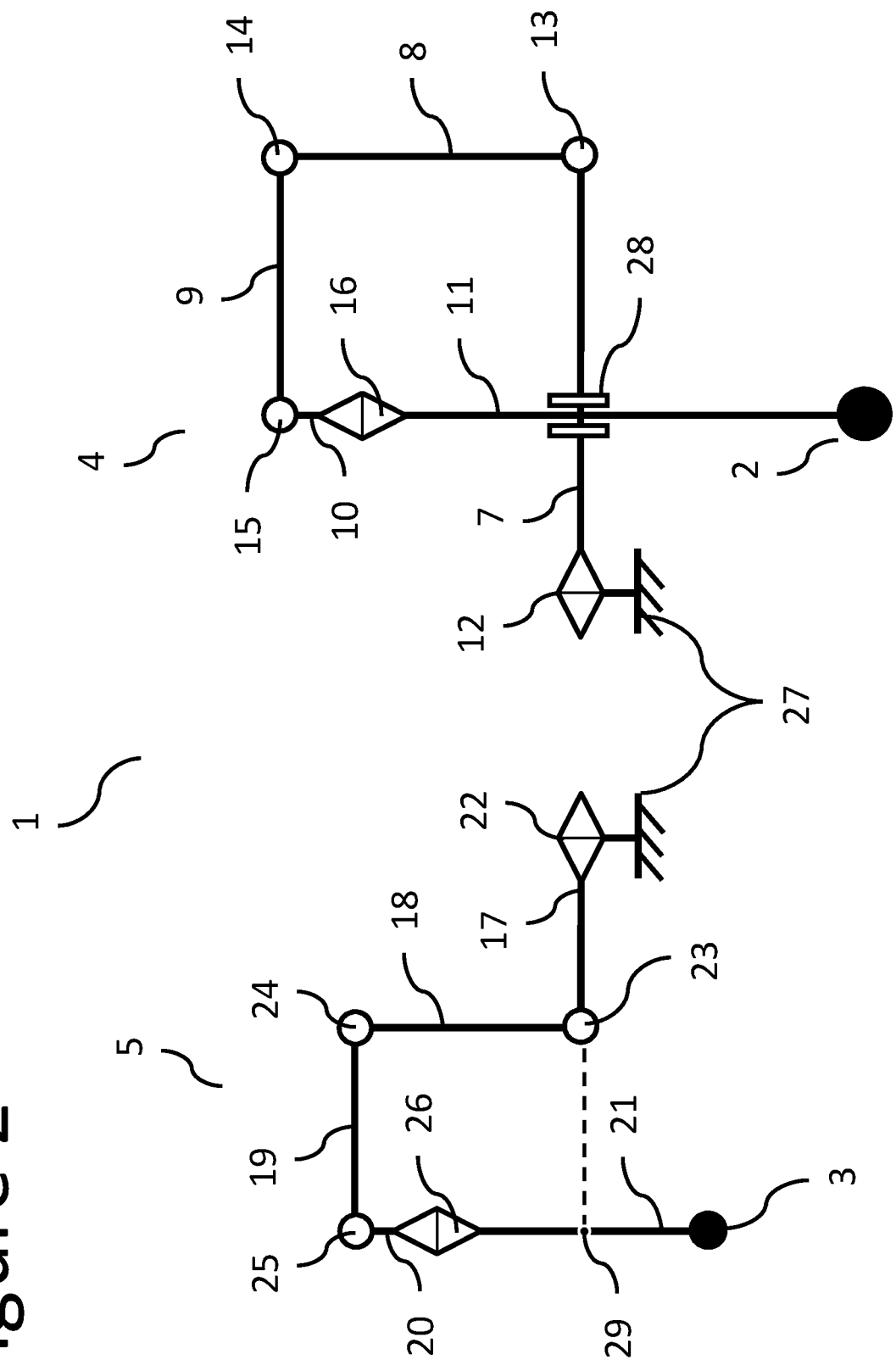
FIG. 2 shows a schematic view of a mechanical telemanipulator according to an embodiment of the invention disclosed in WO2013014621.

According to FIG. 2, the mechanical telemanipulator 1 may comprise: i) a master manipulator 4 having a number of master links 7, 8, 9, 10, 11, rotating over a plurality of master joints 12, 13, 14, 15, 16, a ii) a handle 2 for operating the mechanical telemanipulator 1, connected to the distal end of the master manipulator 4, iii) a slave manipulator 5 having a number of slave links 17, 18, 19, 20, 21 (generally corresponding to the master links 7, 8, 9, 10, 11), and rotating over a plurality of slave joints 22, 23, 24, 25, 26 (generally corresponding to the master joints 12, 13, 14, 15, 16); and iv) an end-effector 3 (instrument/tool or a gripper/holder) connected to the distal end of the slave manipulator 5. More particularly, the kinematic chain formed by the plurality of articulated slave links 17, 18, 19, 20, 21 and corresponding slave joints 22, 23, 24, 25, 26 of the slave manipulator 5, may be substantially identical to the kinematic chain formed by the plurality of articulated master links 7, 8, 9, 10, 11 and corresponding master joints 12, 13, 14, 15, 16 of the master manipulator 4.

Referring still to FIG. 2, the proximal master joint 12 and the proximal slave joint 22 can be considered to be merged in a single joint connecting the mechanical telemanipulator 1 to a ground 27. In the same way, the proximal master link 7 and the proximal slave link 17 can also be considered to be merged in a single connecting link.

The configuration of the mechanical telemanipulator 1 can also be described by considering the end-effector 3 to be part of the slave manipulator 5 and the handle 2 to be part of the master manipulator 4. In a broader sense, the links and joints composing the end-effector 3 can be considered distal slave links and joints, while the links and joints composing the handle 2 can be considered distal master links and joints.

The mechanical telemanipulator 1 further comprises mechanical transmission systems arranged to kinematically connect the slave manipulator 5 with the master manipulator 4 such that the movement (angle of joint) applied on each master joint of the master manipulator 4 is reproduced by the corresponding slave joint of the slave manipulator 5.

For each degree of freedom of the mechanical telemanipulator 1, different types of mechanical transmissions can be used. In order to minimize the system's overall friction, the mechanical transmission between the majority of the master and slave joints is essentially in the form of pulley-routed flexible elements, where each driven pulley of the slave joint is connected to the respective driving pulley of the master joint, by a multi-stage closed cable loop transmission. However, other types of mechanical transmission can be used, comprising rigid and/or geared elements.

Another key feature of the mechanical telemanipulator 1 disclosed in WO2013014621 lies in the mechanical constraint 28 of the mechanical telemanipulator which is configured to constraint movements of the slave manipulator 5 in correspondence with the constraints imposed by an incision realized on a patient. Referring to FIG. 2, in an embodiment of the invention, the mechanical constraint 28 is configured to ensure that, when the mechanical telemanipulator 1 is in operation, the master link 11 of the master manipulator 4 always translates along and rotates about a single point so that the corresponding slave link 21 always translates along and rotates about a fixed point in the space 29, also known as the Remote-Center-of-Motion, RCM.

Therefore, the movement applied on the handle 2, forces the movement of the master joints 12, 13, 14, 15, 16 of the master manipulator 4, by the direct mechanical transmission system and the mechanical constraint 28, to drive the respective movement of the slave joints 22, 23, 24, 25, 26 of the slave manipulator 5. As a result, the multi-articulated end-effector 3 connected to the distal end of the slave manipulator 5 is moved in an equivalent movement of the handle 2, while the slave link 21 always translates along and rotates about the RCM 29.

During a minimally invasive surgical procedure, the RCM 29 is brought in coincidence with the surgical incision point, reducing trauma to the patient and improving cosmetic outcomes of the surgery.

Figure 3:
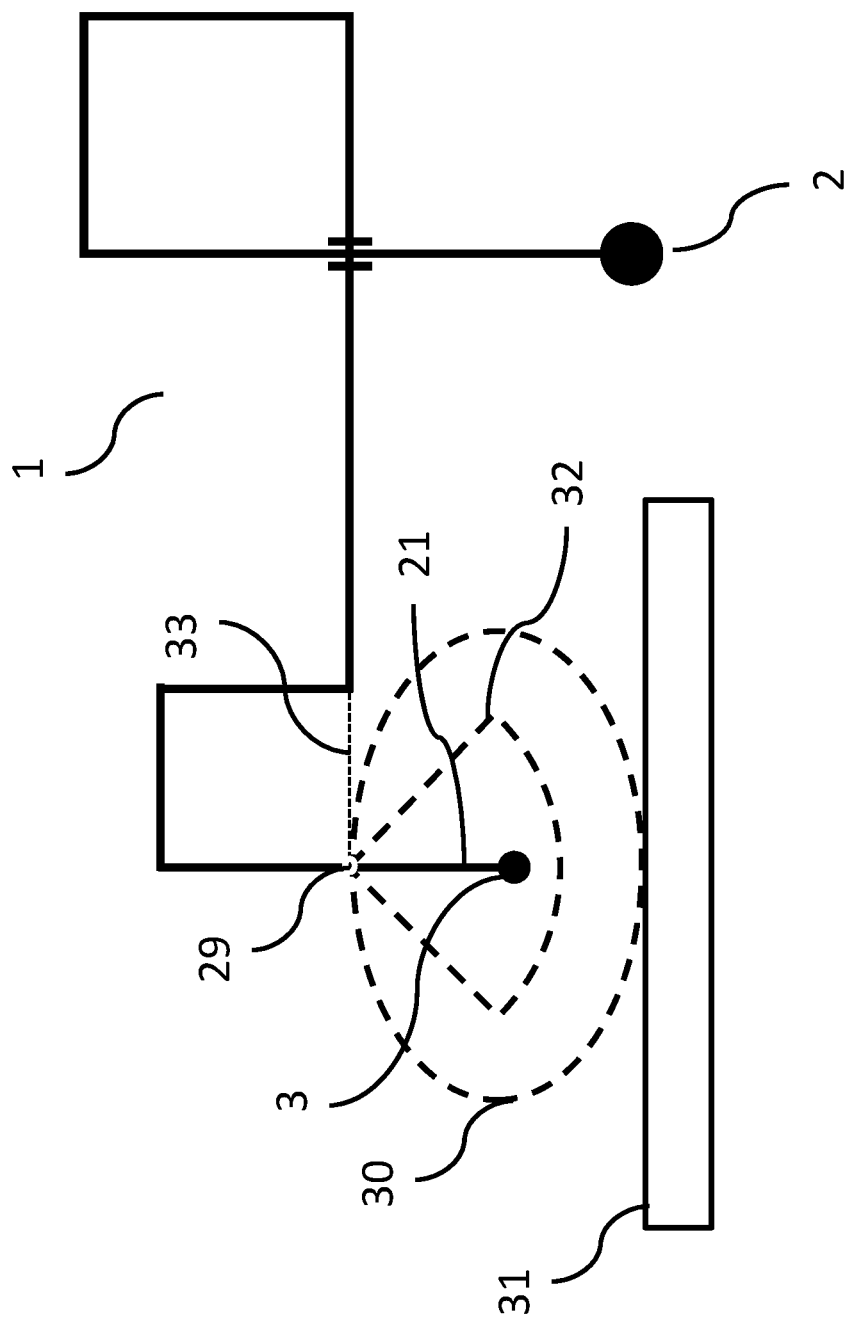
FIG. 3 illustrates some of the limitations of the mechanical telemanipulator according to an embodiment of the invention disclosed in WO2013014621.

Some embodiments of the invention disclosed in WO2013014621 may have a few limitations in terms of its positioning over the patient. As can be seen in FIG. 3, with this specific kinematic model, an alignment 33 between the $1^{st}$ degree-of-freedom, DOF, of the mechanical telemanipulator 1 and the incision 29 on the patient 30 is required. This prerequisite, together with the fact that the neutral position of instrument shaft 21 is perpendicular with the alignment line 33, limits the forward angulation that can be reached inside the patient and forces the distance between the master manipulator 4 and the slave manipulator 5 to be large in order to avoid collisions of the handle 2 with the patient 30 and surgical table 31. In addition, the fact that the handle 2 cannot be positioned over the patient 30, limits the ranges of procedures that can be done.

Figure 4:
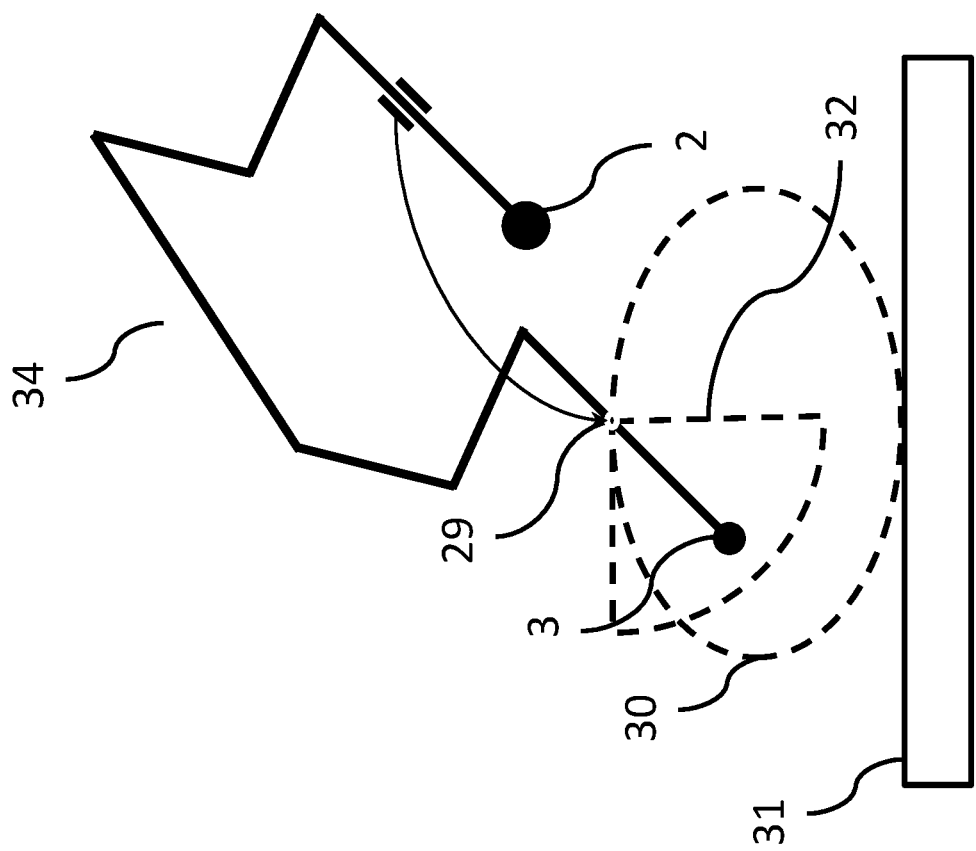
FIG. 4 illustrates some advantages of the mechanical telemanipulator according to an embodiment of the current invention over the mechanical telemanipulator according to an embodiment of the invention disclosed in WO2013014621.

To overcome the above mentioned set of limitations, another embodiment of WO2013014621 can be formulated, as can be seen in FIG. 4. Due to its new kinematics and constraint setup (shown in FIG. 5), with this mechanical telemanipulator 34 the RCM 29 (and therefore the incision point on the patient) doesn't have to be aligned with the first DOF of the mechanical telemanipulator 34 and the neutral position of the instrument shaft 21 doesn't have to be perpendicular with any alignment line. As can be seen in FIG. 4, these features allow for much more flexibility in positioning the mechanical telemanipulator 34 over the patient 30, while allowing shorter distances between the master manipulator 4 and the slave manipulator 5, which results in a lighter and more compact system 1 that can be more easily integrated in the operating room workflow.

Figure 5:
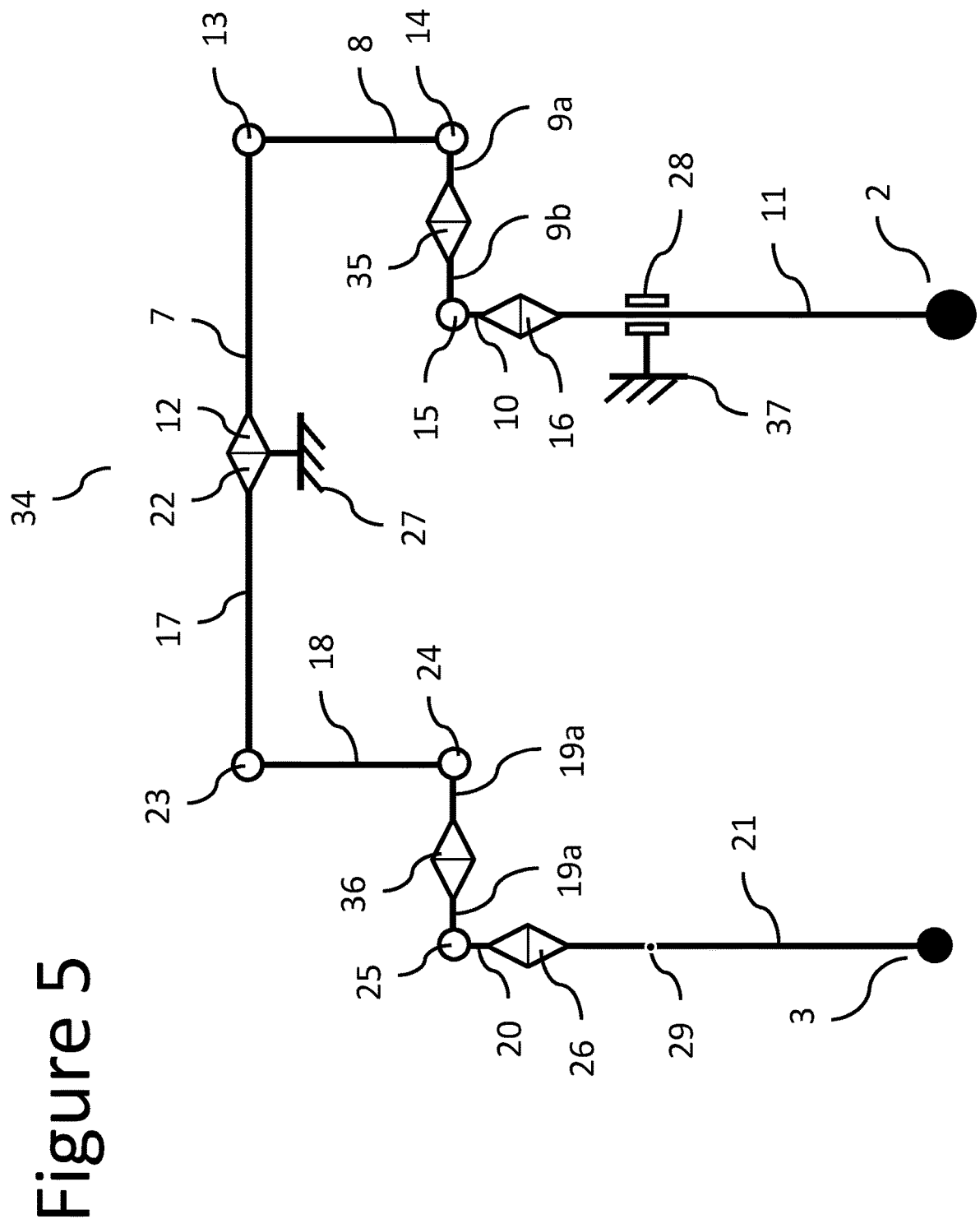
FIG. 5 shows a schematic view of a mechanical telemanipulator according to an embodiment of the current invention.
Figure 6:
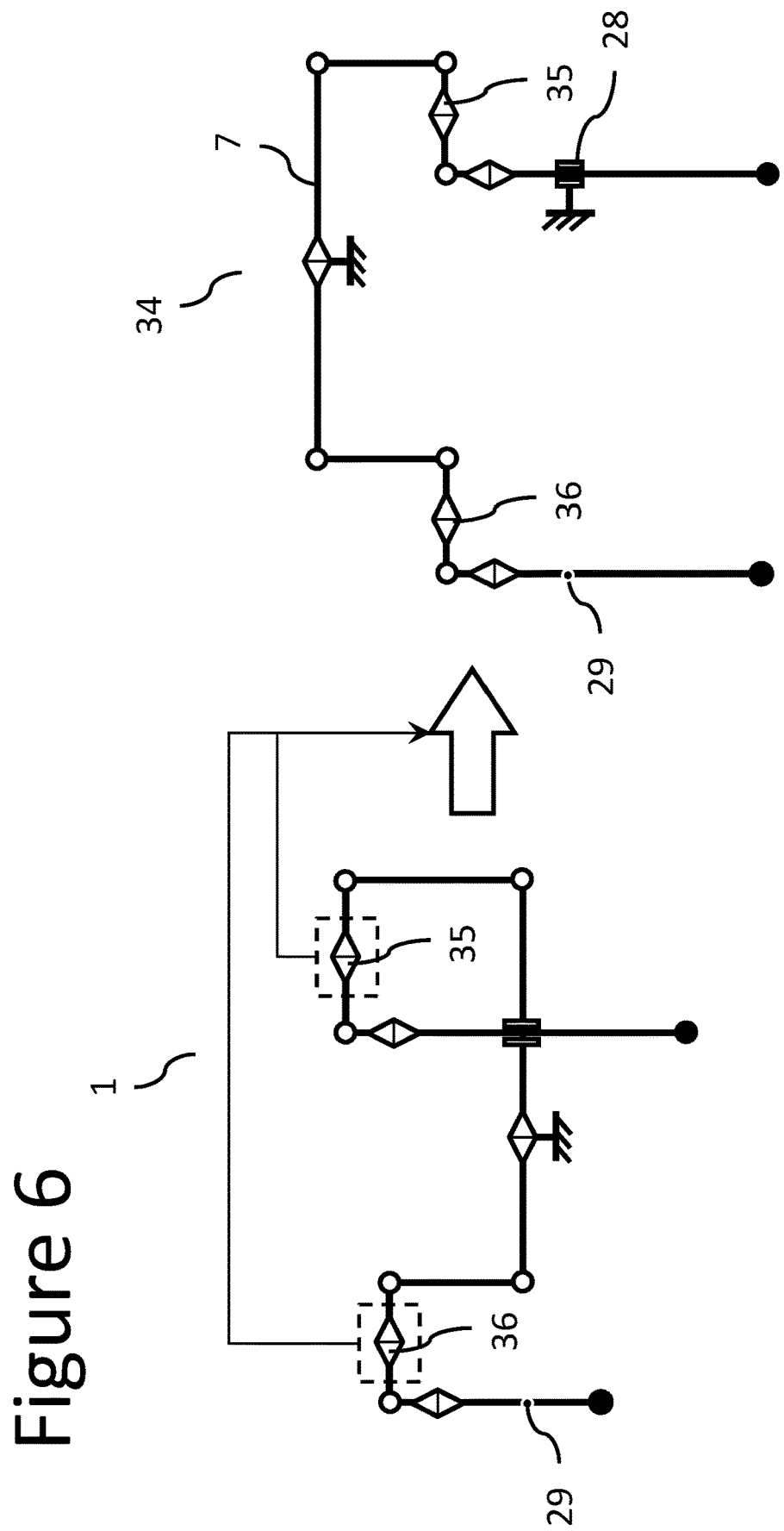
FIG. 6 shows the kinematic and constraint difference between the mechanical telemanipulator according to an embodiment of the current invention and the mechanical telemanipulator according to an embodiment of the invention disclosed in WO2013014621.
Figure 7:
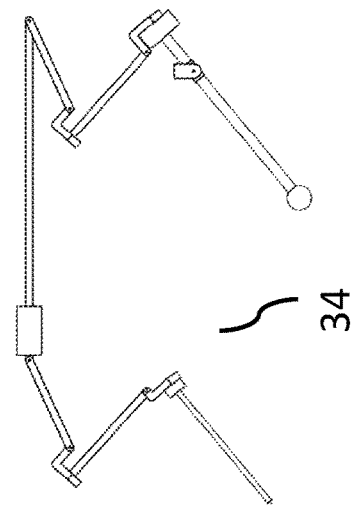
FIG. 7 shows a perspective view of a mechanical telemanipulator according to an embodiment of the current invention in a first active position.
Figure 8:
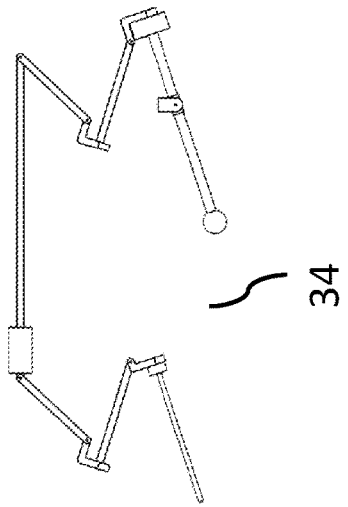
FIG. 8 shows a perspective view of a mechanical telemanipulator according to an embodiment of the current invention in a second active position.
Figure 9:
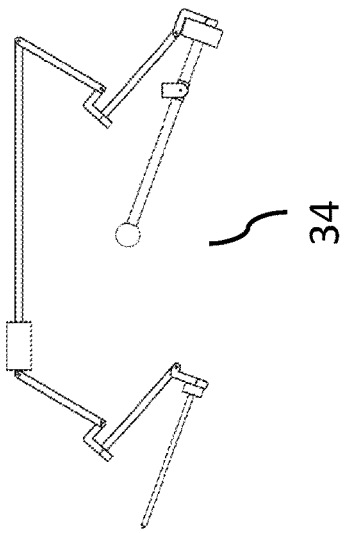
FIG. 9 shows a perspective view of a mechanical telemanipulator according to an embodiment of the current invention in a third active position.
Figure 10:
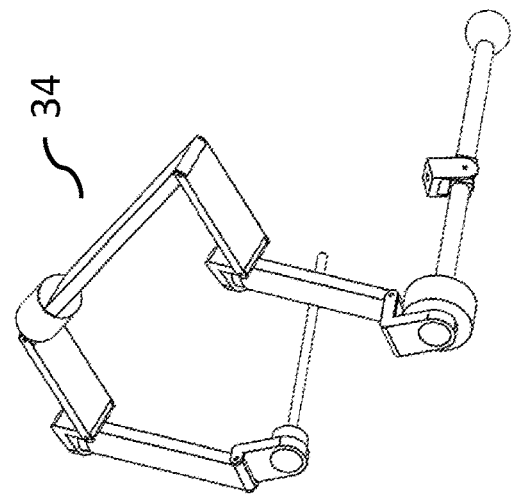
FIG. 10 shows a perspective view of a mechanical telemanipulator according to an embodiment of the current invention in a fourth active position.
Figure 11:
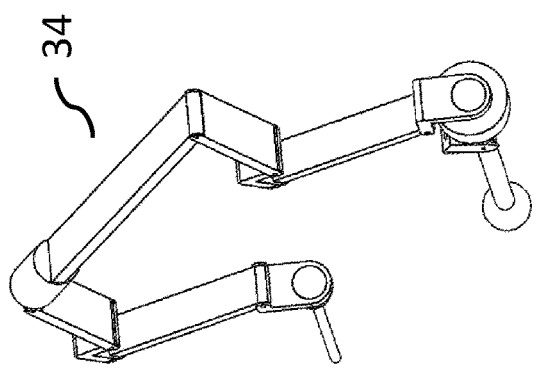
FIG. 11 shows a perspective view of a mechanical telemanipulator according to an embodiment of the current invention in a fifth active position.
Figure 12:
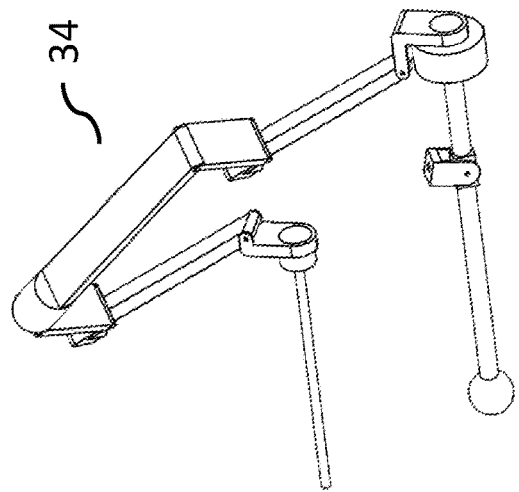
FIG. 12 shows a perspective view of a mechanical telemanipulator according to the preferred embodiment of the current invention in a sixth active position.

FIG. 5 shows the new kinematic model of the system, with a total of 6 degrees-of-freedom (excluding the three degrees-of-freedom of the handle 2 and end-effector 3) and the constraint 28, which is now fixed to a second ground 37 and not to the proximal master link 7, as in the embodiment 1. As can be seen in FIG. 6, this kinematics of the embodiment 34 has one more DOF that the kinematics of the embodiment 1, which consist in the master joint 35 and the correspondent slave joint 36.

FIGS. 7 to 12 show the mechanical telemanipulator 34 in different working configurations.

Figure 13:
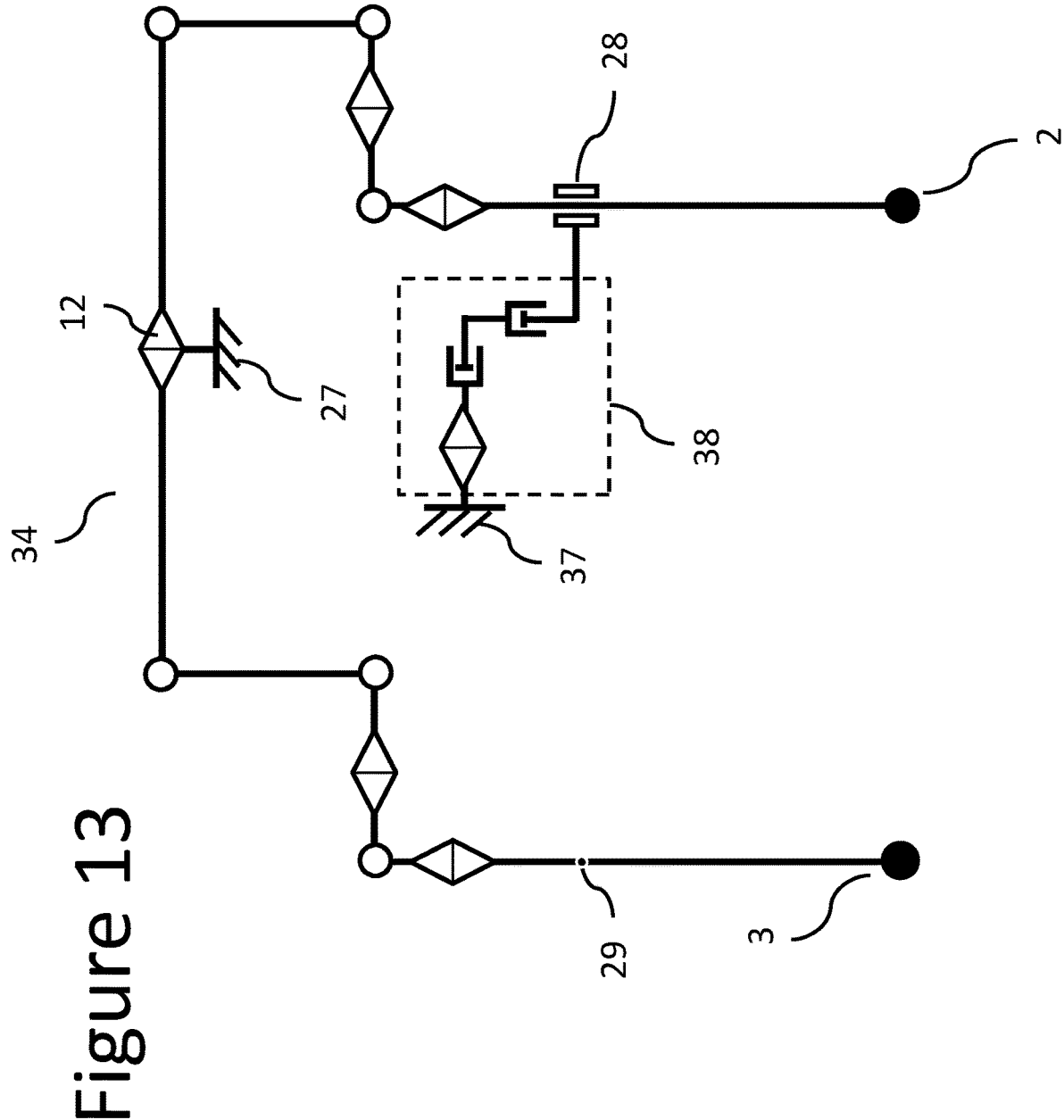
FIG. 13 shows a schematic view of a mechanical telemanipulator according to an embodiment of the current invention where the position of the mechanical constraint can be changed in relation to the ground to which the first degree-of-freedom of the mechanical telemanipulator is attached.
Figure 14:
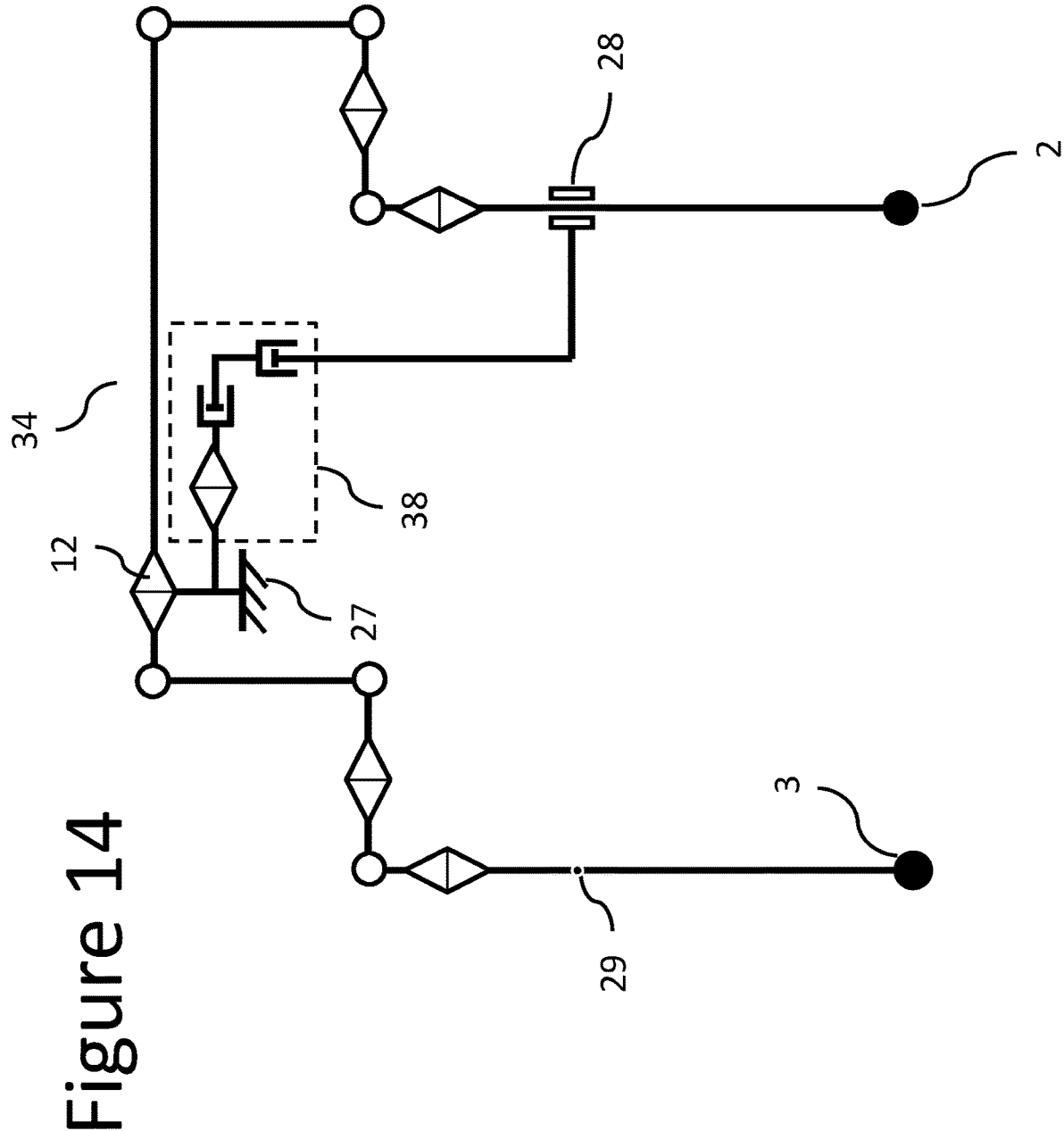
FIG. 14 shows a schematic view of a mechanical telemanipulator according to another embodiment of the current invention where the position of the mechanical constraint can be changed in relation to the ground to which the first degree-of-freedom of the mechanical telemanipulator is attached.

A key feature of this invention consist in the possibility to move the constraint 28 (and therefore the RCM 29) in the 3D space in relation to the ground 27, to which the mechanical telemanipulator 34 is fixed by the first joint 12 (FIGS. 13 and 14). This can be achieved by and articulated system 38 that can be fixed to a second ground 37 (FIG. 13) or directly to the ground 27 (FIG. 14). This feature allows for an increased flexibility in reaching an optimal position of the telemanipulator 34 over the patient, while allowing for a desired workspace inside the patient with an ideal ergonomy for the surgeon.

Figure 15:
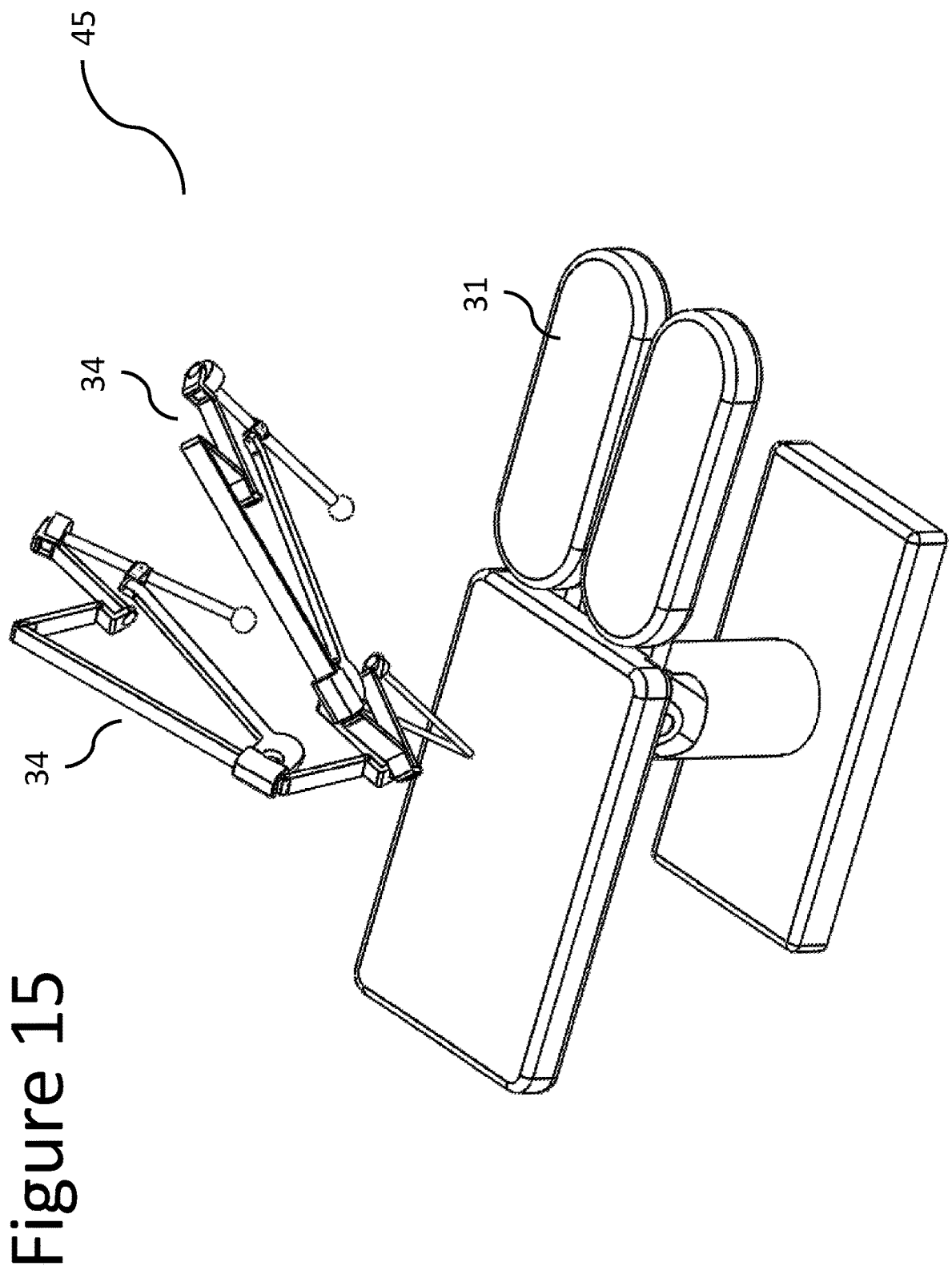
FIG. 15 shows a perspective view of a surgical platform comprising at least one mechanical telemanipulator according to an embodiment of the current invention.

A surgical platform 45, which comprises at least one mechanical telemanipulator 34, can be seen in FIG. 15. It is arranged in a way that the mechanical telemanipulators 34 can be placed over the surgical table 31, while having their RCM 39 merged with the incision points in the patient.

Figure 16:
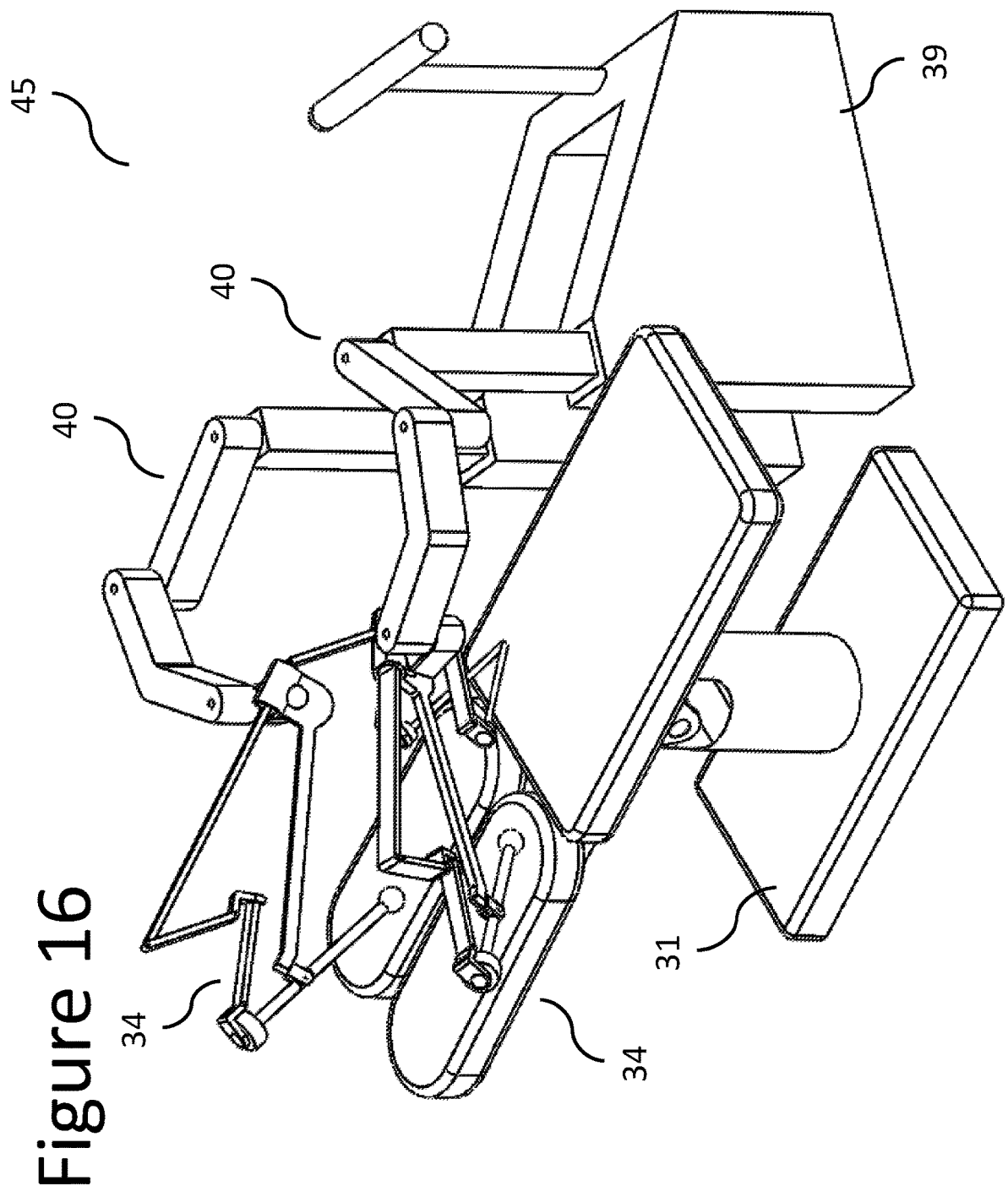
FIG. 16 shows a perspective view of a surgical platform comprising at least one mechanical telemanipulator according to an embodiment of the current invention, a movable base and at least one articulated positioning manipulator.
Figure 17:
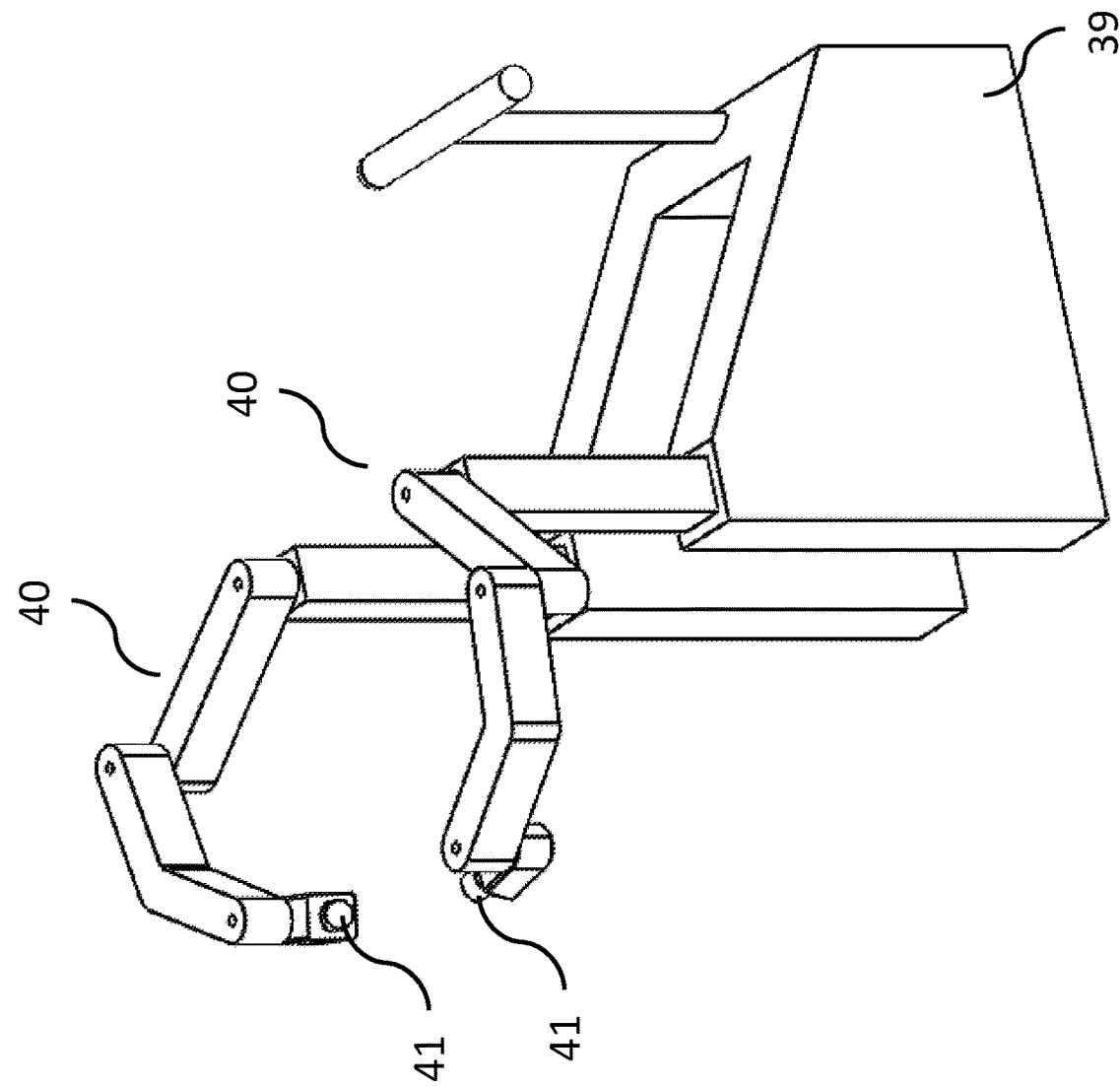
FIG. 17 shows a perspective view of the movable base and at least one articulated positioning manipulator of the surgical platform of FIG. 16.

According to FIGS. 16 and 17, the surgical platform 45, may further comprise a movable base 39, and at least one articulated positioning manipulator 40, whose distal extremity 41 is fixed to the mechanical telemanipulator 34 so that it can be moved over the surgical table 31 and stably fixed in specific positions of the 3D space. In other embodiments of the current invention, instead of a single movable base 39, each one of the two articulated positioning manipulators 40 may be mounted on a separate movable base, independent from the movable base of the other articulated positioning manipulator 40.

Figure 18:
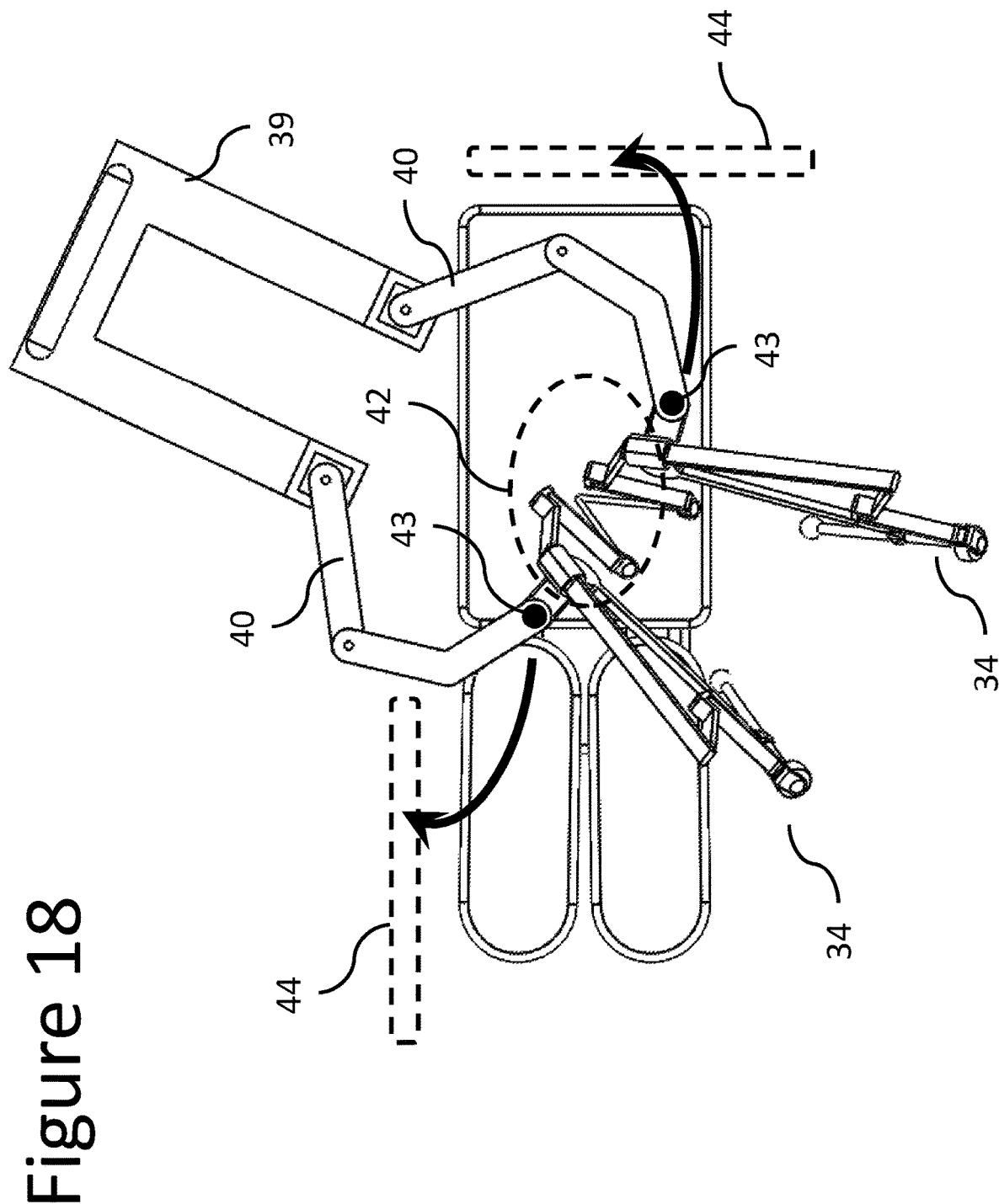
FIG. 18 illustrates a first solution of how the mechanical telemanipulators of the surgical platform of FIG. 16 can be removed from the surgical area during a surgical procedure.
Figure 19:
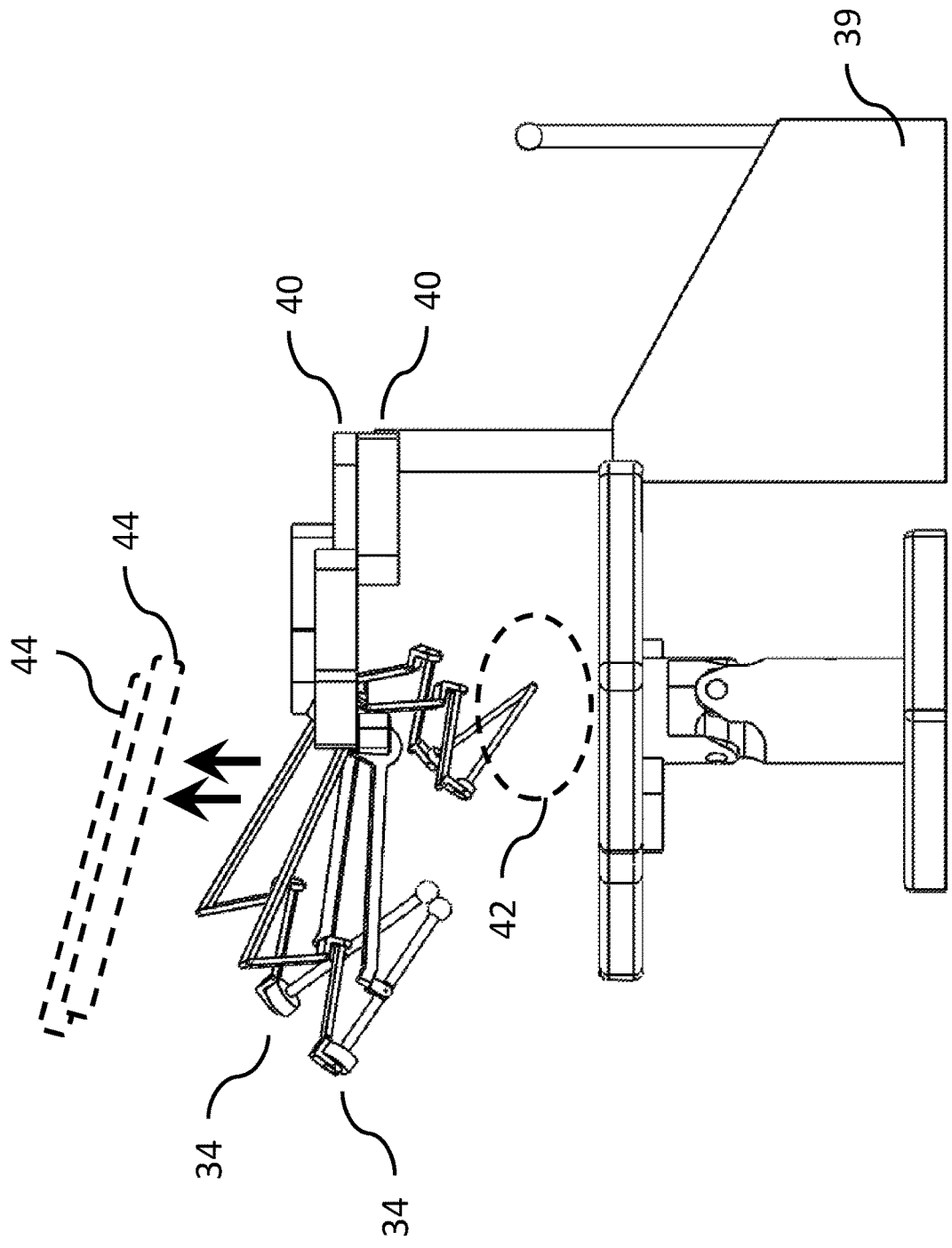
FIG. 19 illustrates a second solution of how the mechanical telemanipulators of the surgical platform of FIG. 16 can be removed from the surgical area during a surgical procedure.

Each articulated positioning manipulator 40 should be gravity-compensated (together with the mechanical telemanipulator 34 that is being carried) by means of systems of counterweights and/or springs. In addition, each articulated positioning manipulator 40 should be provided with a system of clutches/brakes on each one of the joints so that they are blocked by default and can be released and moved when a switch 43 is pressed. By pressing the switch 43, the mechanical telemanipulator 34 can be moved in the 3D space to be positioned over the patient or to be removed from the surgical area 42 to a remote location 44, in particular during a surgical procedure (FIGS. 18 and 19) but also before or after. This feature is critical for an easy integration of the surgical platform with the operating room workflow, were the mechanical telemanipulators can be used interactively with other types of surgical instrumentation (for instance, standard laparoscopic instruments) during the same surgical procedure.

Figure 24:
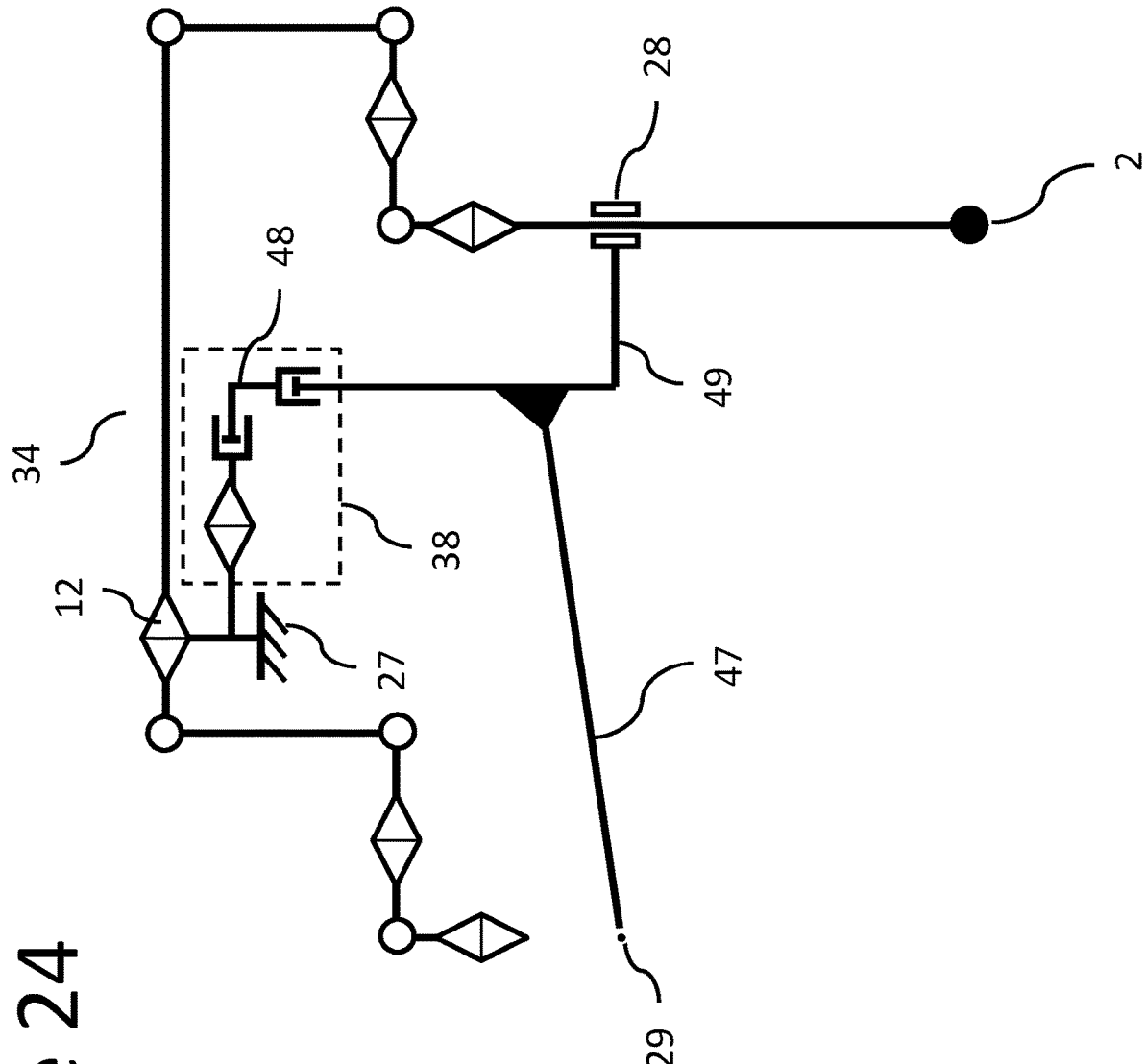
FIG. 24 shows the kinematic model of an embodiment of the current invention where an incision pointer is mounted on the mechanical telemanipulator so that the RCM can be localized and precisely with the body incision of the patient.

In order to be precisely positioned over the patient and aligned with the body incision of the patient, an incision pointer 47 (FIG. 24) can be mounted on each mechanical telemanipulator 34 during their positioning over the patient, when the detachable instrument containing the end-effector 3 is still not mounted on the mechanical telemanipulator 34. As can be seen in FIG. 24, the incision pointer 47 can be rigidly attached to the distal moving link 49 of the articulated system 38 so that its distal extremity is pointing to the RCM 29 of the mechanical telemanipulator 34 (whose 3D position with respect to the ground 27 is changing according to the positional configuration of the articulated system 38). Then, as soon as the distal extremity of the incision pointer 47 is brought to be substantially coincident to the incision of the patient body (where a surgical trocar may be in place) the 3D position of the mechanical telemanipulator 34 is blocked in the 3D space but releasing the switch 43 of the articulated positioning manipulator 40.

Figure 21:
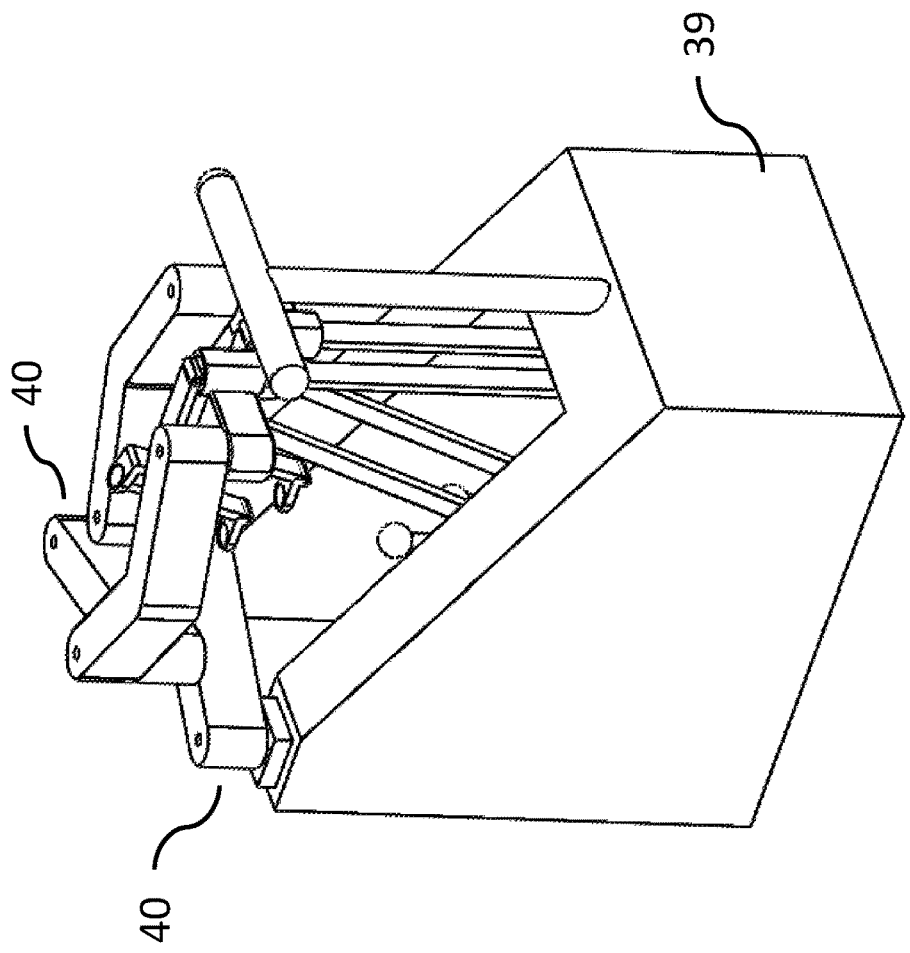
FIG. 21 shows a second perspective view of the surgical platform of FIG. 16 in a "compact storage" configuration.
Figure 20:
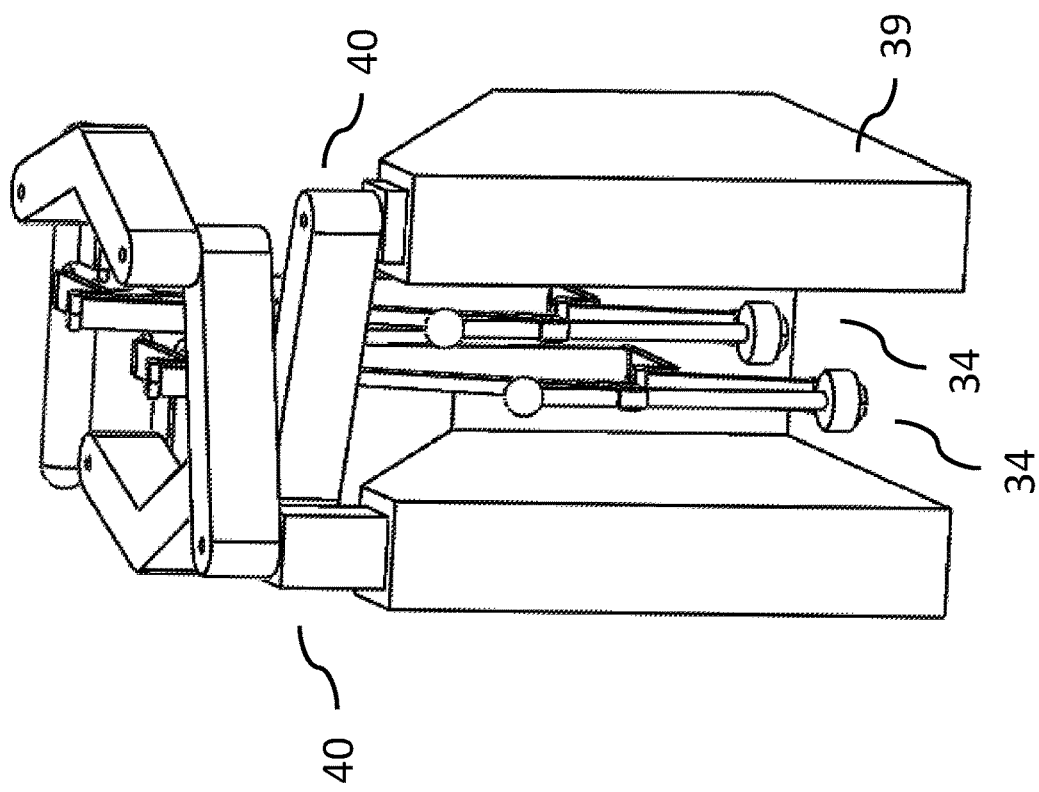
FIG. 20 shows a first perspective view of the surgical platform of FIG. 16 in a "compact storage" configuration.

As shown in FIGS. 20 and 21, the surgical platform 45 allows for a compact storing position, where the mechanical telemanipulators 34 are brought by the articulated positioning manipulators 40 to a protected location over the platform's movable base 39. In the shown embodiment, the position of both telemanipulators is substantially vertical but in other embodiments of the current invention they may be in other special configurations (for instance, substantially horizontal).

Figure 25:
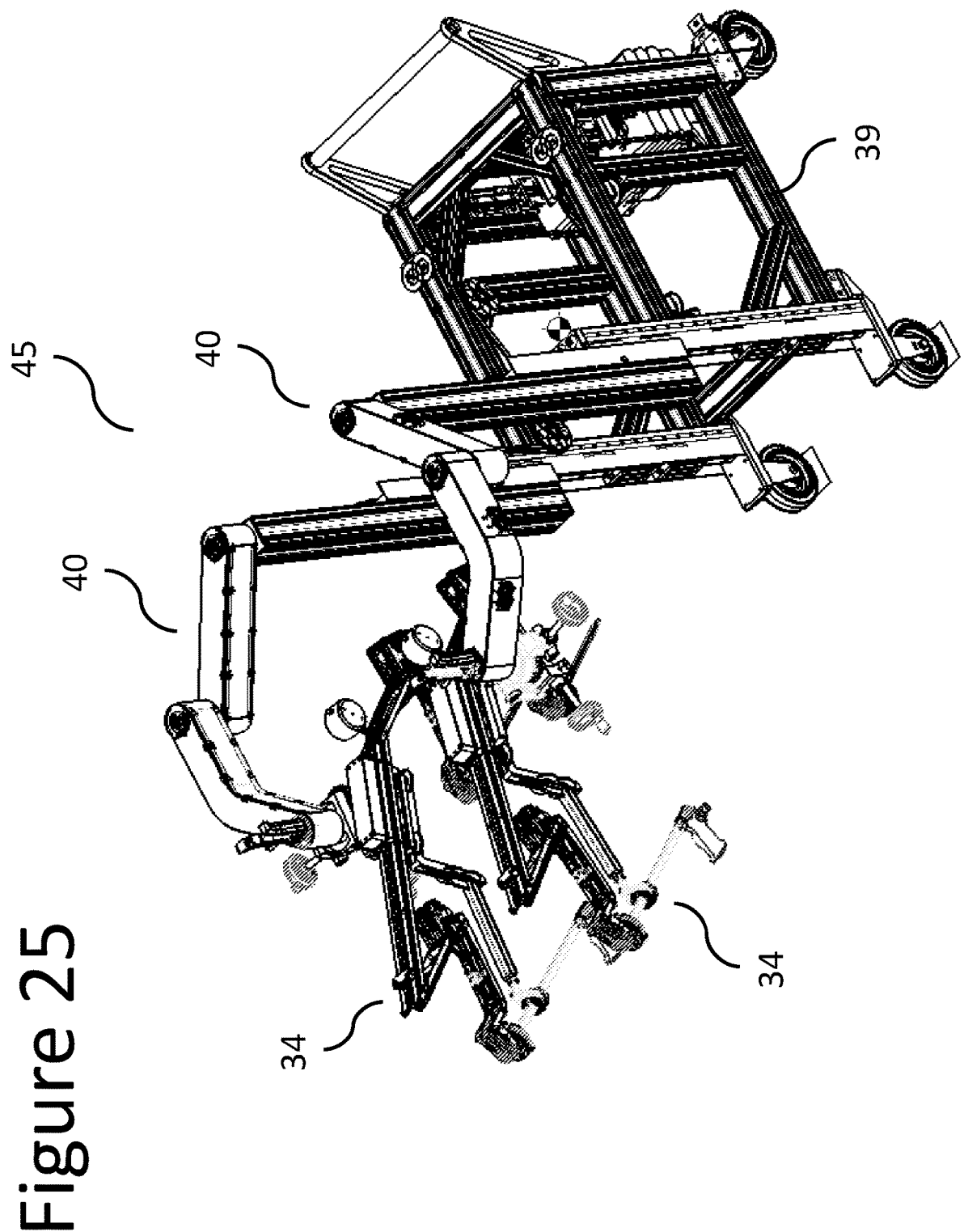
FIGS. 25 and 26 show two different views of the surgical platform, in a detailed stage of design, using two mechanical telemanipulators according to an embodiment of the current invention.
Figure 26:
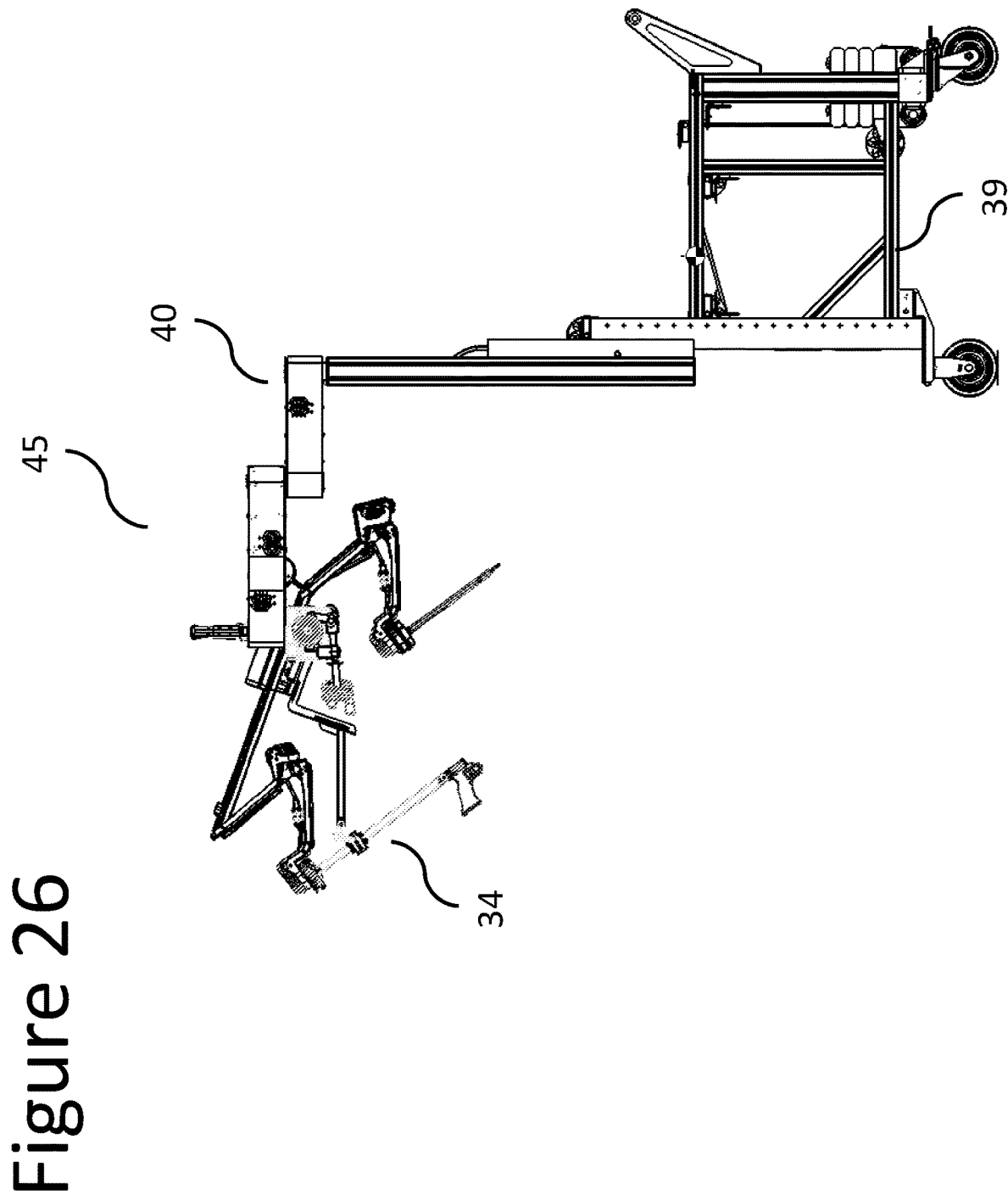
Figure 27:
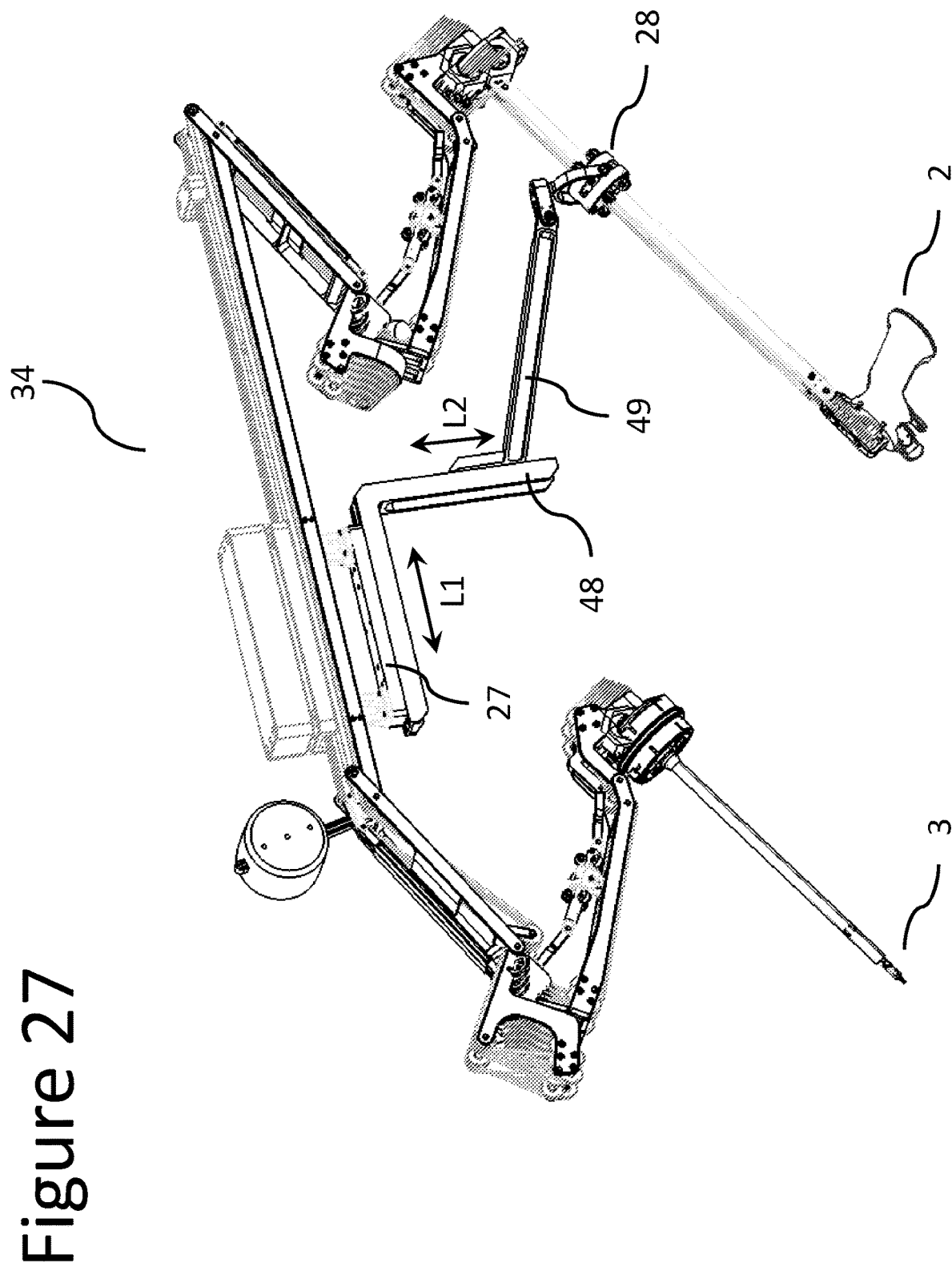
FIG. 27 shows a perspective view of a mechanical telemanipulator, in a detailed stage of design, according to an embodiment of the current invention.

FIGS. 25 and 26 show two different views of the surgical platform 45 in a more detailed stage of design, while FIG. 27 shows an embodiment of the current invention, used on the mechanical telemanipulator 34, where the articulated system 38 provides 2 degrees-of-freedom L1, L2 (corresponding to the linear displacement between the link 48 and the ground 27 and the linear displacement between the distal link 49 and the link 48) to the constraint 28.

Figure 22:
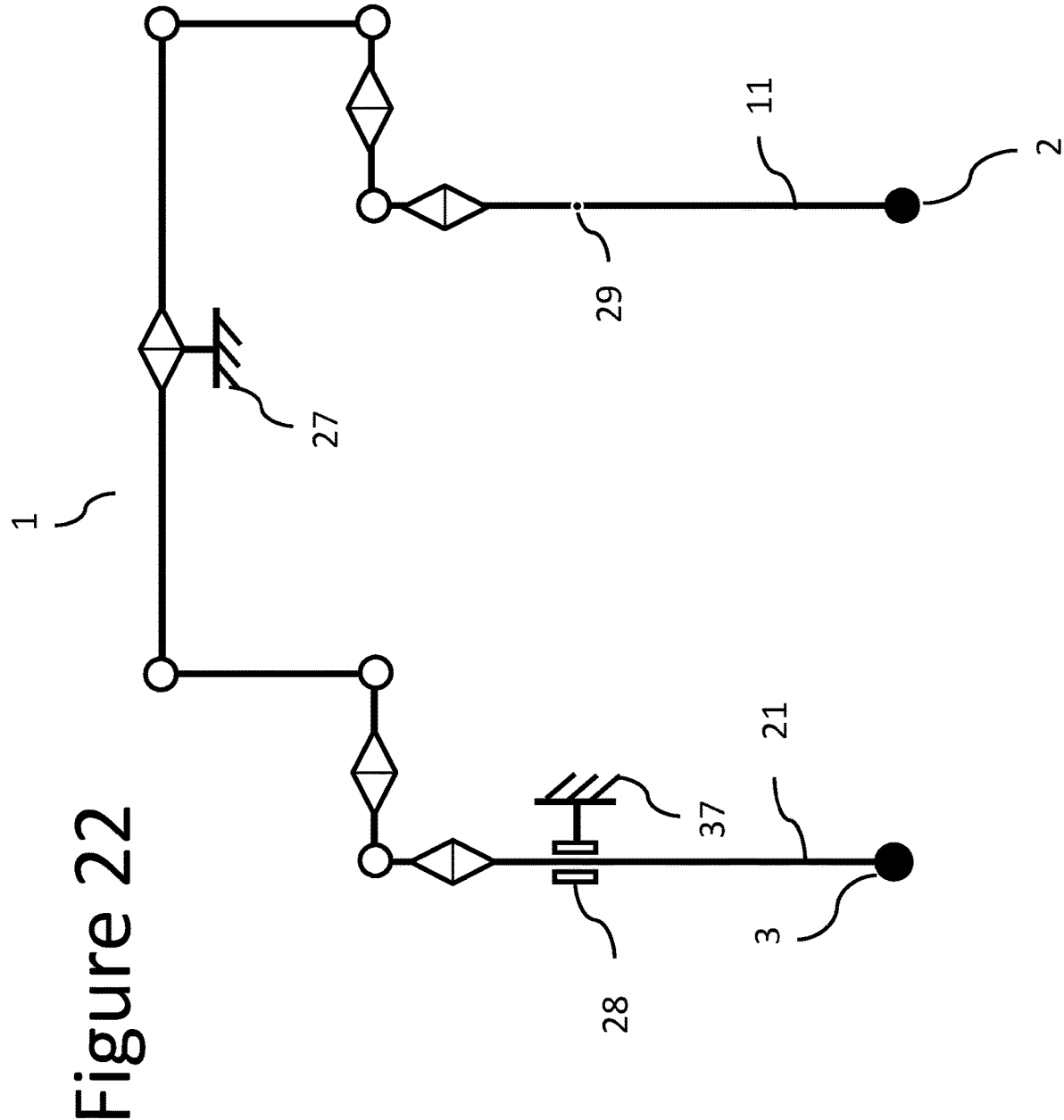
FIG. 22 shows the kinematics of a mechanical telemanipulator having a constraint on the slave manipulator and a RCM on the master manipulator according to an embodiment of the present invention.
Figure 23:
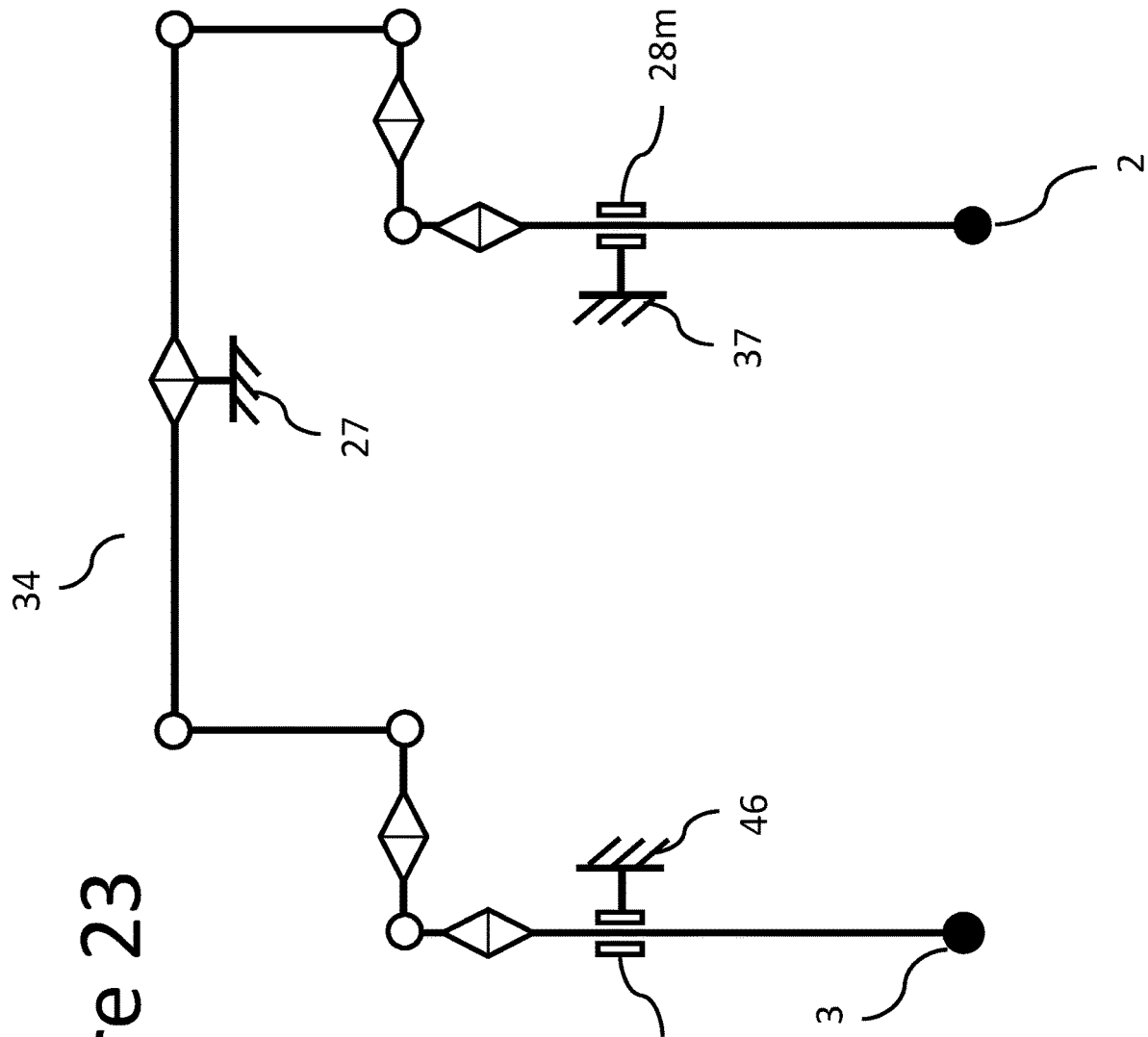
FIG. 23 shows the kinematics of a mechanical telemanipulator with constraints on both the master and slave manipulator according to an embodiment of the present invention.

While this invention has been shown and described with reference to particular embodiments thereof, it will be understood by those skilled in the art that various changes in form and details may be made therein without departing from the spirit and scope of the invention as defined by the appended claims. For instance, knowing that each master joint 12, 13, 14, 35, 15, 16 is kinematically connected with the corresponding slave joint 22, 23, 24, 36, 25, 26 another embodiment of the current invention can be achieved by placing the constraint 28 on a slave link 21 to have the RCM 29 on the master manipulator 4, around which the master link 11 would always rotate about and translate along (FIG. 22). Similarly, a different embodiment of the present invention could be reached by having the constraint 28m in the master link 11 and placing a second constraint 28s on the slave manipulator 5 (FIG. 23), so that the slave link 21 would always rotate about and translate along a point that is coincident with the incision.

The invention claimed is:

1. A surgical telemanipulator for remote manipulation to perform a surgery, the surgical telemanipulator comprising:
a slave manipulator having a number of slave links interconnected by a plurality of slave joints;
an end-effector connected to the slave manipulator to be moved responsive to movement at the slave manipulator to perform the surgery;
a master manipulator having a corresponding number of master links interconnected by a plurality of master joints;
a handle connected to the master manipulator for operating the surgical telemanipulator;
a first transmission arranged to operatively connect the slave manipulator with the master manipulator such that the movement applied on each master joint of the master unit is reproduced by the corresponding slave joint of the slave manipulator;
a second transmission arranged to operatively connect the end-effector with the handle such that the movements applied on the handle cause corresponding movements at the end-effector;
at least one mechanical constraint applied on a master link of the master manipulator such that the master link is guided through the at least one mechanical constraint to translate along and rotate about a stationary single point so that the corresponding slave link of the slave manipulator always translates along and rotates about a remote center-of-motion when the surgical telemanipulator is operated; and
an articulated system coupled to a stationary ground, the articulated system having at least one degree-of-freedom and comprising at least one moving link,
wherein the at least one mechanical constraint is mounted on the at least one moving link of the articulated system so that the at least one mechanical constraint and accordingly the remote center-of-motion of the slave manipulator are movable in three dimensions relative to the stationary ground,
wherein a kinematic model of a chain formed by the plurality of slave links and corresponding slave joints of the slave manipulator, is identical to a kinematic model of a chain formed by the plurality of master links and corresponding master joints of the master manipulator, and
wherein the first transmission is configured such that each slave link of the slave manipulator and the corresponding master link of the master manipulator move parallel to each other when the surgical telemanipulator is operated.

2. The surgical telemanipulator of claim 1, wherein the articulated system has two degrees-of-freedom.

3. The surgical telemanipulator of claim 1, further comprising a second mechanical constraint applied on a slave link to enable the corresponding master link to translate along and rotate about a remote center of motion.

4. The surgical telemanipulator of claim 1, wherein an incision pointer is attached to a link of the at least one moving link of the articulated system to identify the location of the remote center of motion.

5. The surgical telemanipulator of claim 1, wherein an amplitude of movement of a distal extremity of a distal master link of the master manipulator, when the surgical telemanipulator is operated, is reproduced by a distal extremity of a distal slave link of the slave manipulator at a predetermined scale ratio which corresponds to a ratio between a length of each slave link and a length of the corresponding master link.

6. A surgical platform comprising at least two surgical telemanipulators of claim 1, wherein each surgical telemanipulator is mounted on an articulated positioning manipulator, and wherein each surgical telemanipulator is configured to be operated independently from the other.

7. The surgical platform of claim 6, wherein each articulated positioning manipulator is connected to a separate movable base.

8. The surgical platform of claim 6, wherein each articulated positioning manipulator is connected to a single movable base.

9. The surgical platform of claim 6, wherein each articulated positioning manipulator comprises an adjustment element to position the remote center of motion of each surgical telemanipulator in correspondence with a surgical incision realized on a patient.

10. The surgical platform of claim 6, wherein each articulated positioning manipulator is gravity-compensated by a system of counterweights and/or springs so that it can be more easily moved by the users.

11. The surgical platform of claim 6, wherein each articulate positioning manipulator comprises one or more joints, and wherein each articulated positioning manipulator comprises a system of clutches/brakes on each one of the one or more joints so that the joints are blocked by default and can be released and moved when a switch is pressed.

12. The surgical platform of claim 6, wherein each articulated positioning manipulator can bring each surgical telemanipulator to a protected location when the surgical telemanipulators are not in operation.

* * * * *